US008517942B2

(12) United States Patent
Hill

(10) Patent No.: US 8,517,942 B2
(45) Date of Patent: *Aug. 27, 2013

(54) METHOD FOR NON-INVASIVE DETERMINATION OF GLYCOGEN STORES

(76) Inventor: John C. Hill, Denver, CO (US)

( * ) Notice: Subject to any disclaimer, the term of this patent is extended or adjusted under 35 U.S.C. 154(b) by 205 days.

This patent is subject to a terminal disclaimer.

(21) Appl. No.: 13/159,135

(22) Filed: Jun. 13, 2011

(65) Prior Publication Data

US 2011/0319735 A1 Dec. 29, 2011

Related U.S. Application Data

(60) Provisional application No. 61/358,778, filed on Jun. 25, 2010.

(51) Int. Cl.
*A61B 5/00* (2006.01)

(52) U.S. Cl.
USPC .......................................... 600/365; 600/438

(58) Field of Classification Search
USPC .......... 600/309, 365, 437–472; 382/128–134
See application file for complete search history.

(56) References Cited

U.S. PATENT DOCUMENTS

| 4,831,527 | A | * | 5/1989 | Clark | 600/553 |
| 5,670,135 | A | | 9/1997 | Schroder | |
| 7,683,617 | B2 | | 3/2010 | Van Zijl et al. | |
| 2003/0018257 | A1 | * | 1/2003 | Hsu et al. | 600/442 |

OTHER PUBLICATIONS

Price, et al. "Effect of muscle glycogen content on exercise-induced changes in muscle T2 times." Journal of Applied Physiology 84.4 (1998): 1178-1184.*
Nguyen, et al. "Contrast-enhanced ultrasonography in patients with glycogen storage disease type la and adenomas." Journal of Ultrasound in Medicine 28.4 (2009): 497-505.*
Gabriel, et al. "Ultrasound of the abdomen in endurance athletes." European journal of applied physiology and occupational physiology 73.1 (1996): 191-193.*
Steensberg, Adam, et al. "Muscle glycogen content and glucose uptake during exercise in humans: influence of prior exercise and dietary manipulation." The Journal of physiology 541.1 (2004): 273-281.*
Kadah, et al. "Classification algorithms for quantitative tissue characterization of diffuse liver disease from ultrasound images." Medical Imaging, IEEE Transactions on 15.4 (1996): 466-478.*

* cited by examiner

*Primary Examiner* — Charles A Marmor, II
*Assistant Examiner* — Mitchell Alter
(74) *Attorney, Agent, or Firm* — Daniel W. Roberts; Law Offices of Daniel W. Roberts, LLC

(57) ABSTRACT

Provided is a non-invasive method of determining glycogen stores including: receiving an ultrasound scan of at least a portion of a target muscle; and evaluating at least a portion of the ultrasound scan to determine glycogen store within the target muscle.

50 Claims, 16 Drawing Sheets

FIG. 14
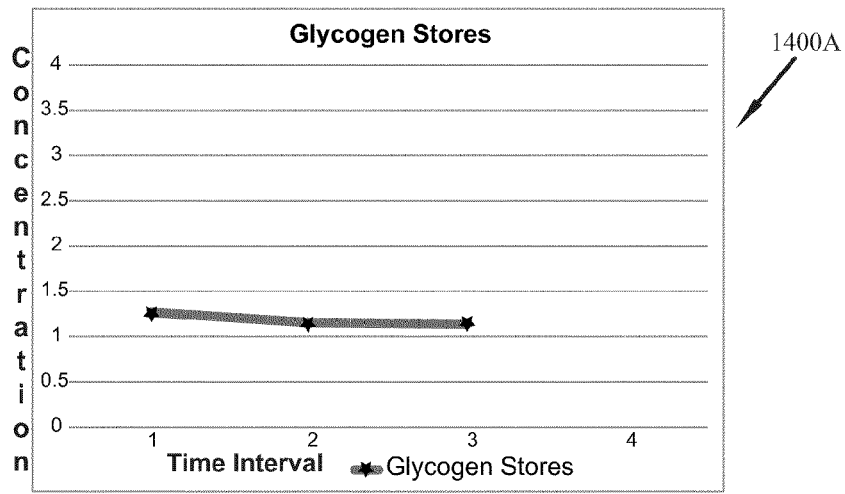
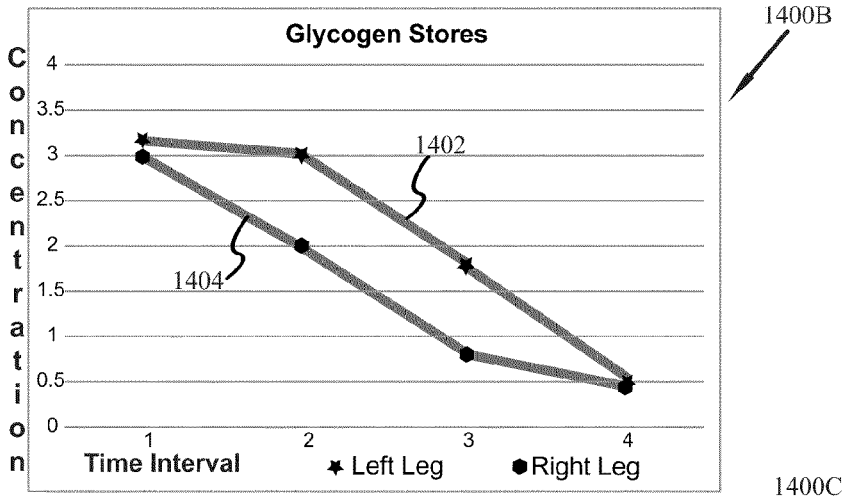
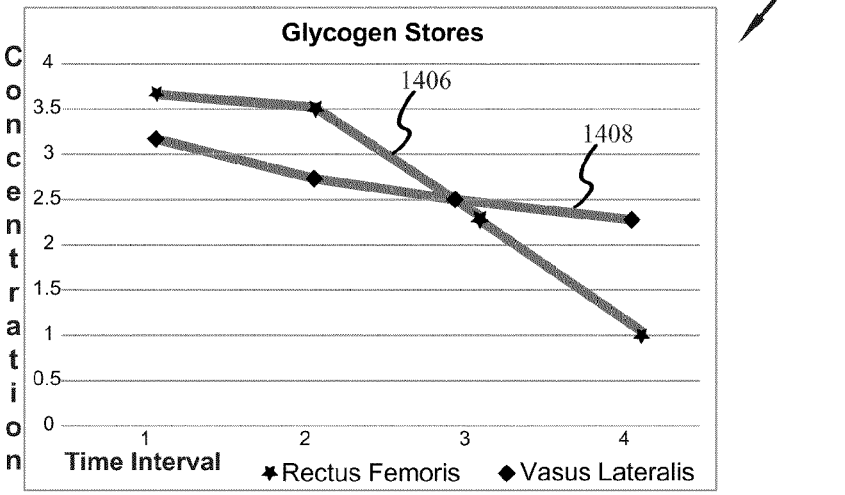

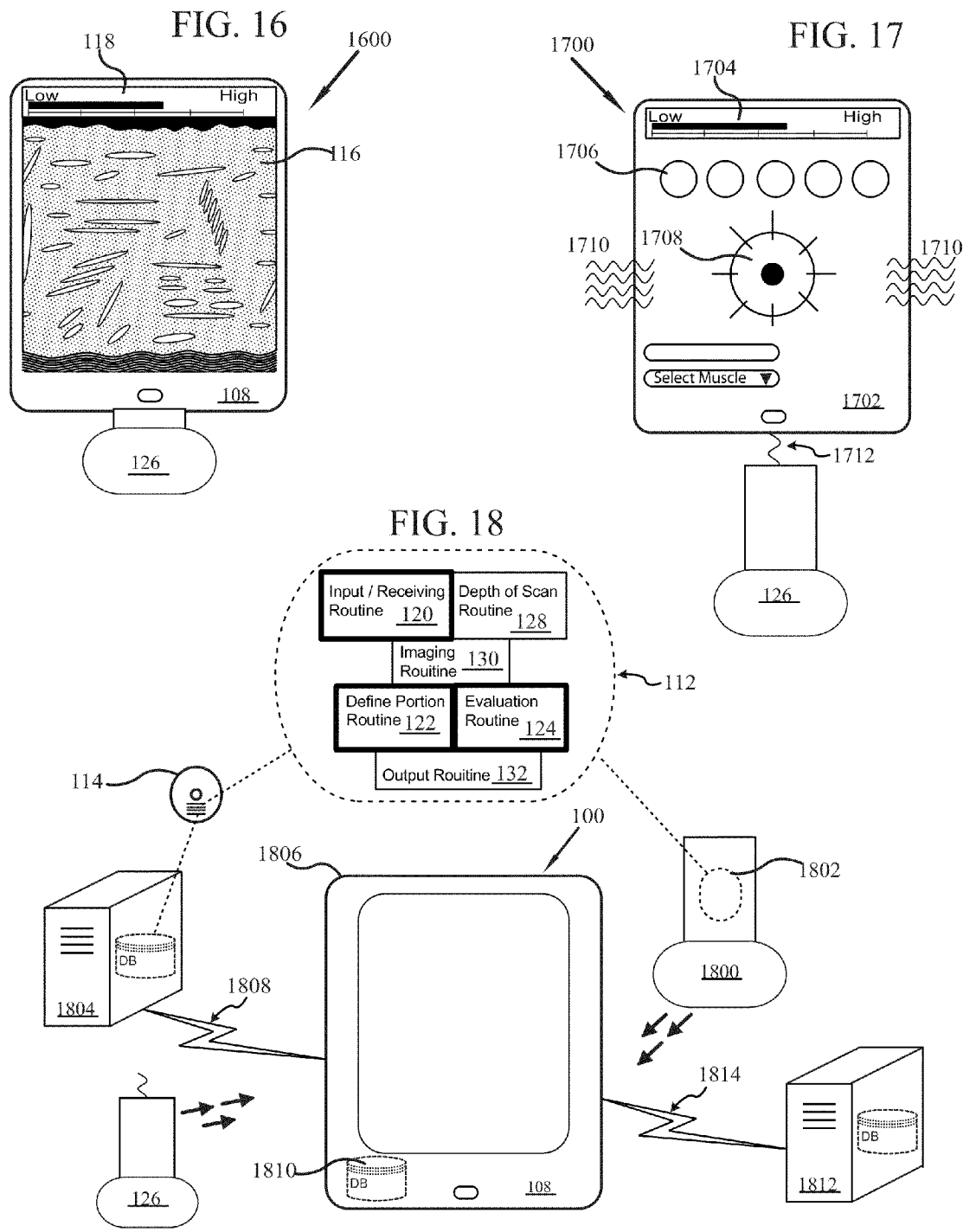

METHOD FOR NON-INVASIVE DETERMINATION OF GLYCOGEN STORES

CROSS REFERENCE TO RELATED APPLICATIONS

This application claims the benefit under 35 U.S.C. §119 (e) of U.S. Provisional Application No. 61/358,778 filed Jun. 25, 2010, the disclosure of which is incorporated herein by reference.

FIELD OF THE INVENTION

The present invention relates generally to the determination of glycogen stores in animal and human tissue, and more specifically to the non-invasive determination of muscle glycogen stores.

BACKGROUND

Glycogen is the storage form of glucose in animal and human tissues. Moreover it is the polysaccharide molecule that functions as the secondary long-term energy store in animal cell tissue and may be represented as $(C_6H_{10}O_5)_n$. Glycogen is made up of glucose building blocks, glucose $(C_6H_{12}O_6)$ being a monosaccharide, or simple sugar and an important carbohydrate in biology. Glycogen is made primarily by the liver and the muscles, but it can also be made by glycogenesis within the brain and stomach. Glycogen is analogous to starch in plants, and is commonly referred to as animal starch, having a similar structure to amylopectin.

Glycogen plays an important role in the glucose cycle as it forms an energy reserve that can be metabolized quickly to meet a sudden need for glucose. Generally, it is the glycogen stored in the liver that is made accessible to other organs and muscles. Muscles themselves utilize their own stores before drawing from the liver. Within the muscle, glycogen is generally found in low concentrations, about 1~2% of the muscle mass. However, the amount of glycogen stored in a person's body largely is dependent on physical training, metabolic rate and eating habits.

When a meal containing carbohydrates is eaten and digested, blood glucose levels rise and the pancreas releases insulin. Blood glucose enters the liver cells and the insulin acts upon the liver cells to stimulate the action of enzymes including glycogen synthase. Glucose molecules are added together in chains of glycogen so long as the levels of both insulin and glucose remain plentiful. When needed for energy, the glycogen chains are deconstructed and converted back to glucose.

With respect to muscle tissues, glycogen stores within the muscle function as an immediate reserve of energy for the muscle, however muscle cells lack the specific enzyme glucose-6-phosphatase that is required to pass glucose into the blood. As such the glycogen stores within a muscle are for the use of that particular muscle and not shared.

Long distance and endurance athletes such as cyclists, marathon runners and triathletes frequently experience glycogen debt wherein nearly all of the athlete's glycogen stores are depleted after long periods of exertion without sufficient energy replacement through intake of foods and supplements. A phenomena commonly referred to as "hitting the wall" it is an experience most amateur and pro athletes seek to avoid for it's onset usually signals the end of good performance, if not the simple ability to continue participation in the activity.

Developing glycogen stores in the muscles themselves is highly desirable for many amateur and pro athletes, for the muscle glycogen stores are immediately available and do not have to be delivered by the circulation of blood from the liver. Significant training and dietary structure can and often is dedicated towards the development and conditioning of muscles to produce and store high quantities of glycogen.

How much glycogen is present at the start of an event can therefore be a significant factor in how a person will perform. For the pro athlete as well as many amateur athletes, knowledge regarding their glycogen stores, specifically the muscle glycogen stores of key muscles is highly desirable.

If the stores can be identified as being low, the person can proactively eat more carbohydrates. If the stores can be identified as being good, the person can avoid excessive eating—and therefore avoid having blood taken from the muscles to the stomach for digestion, as well as the potentially excess weight of the food or liquids providing the carbohydrates. More simply put it is important to eat enough but not too much, yet where that balance point is can shift throughout the day and from day to day.

Present methods for measuring glycogen involve the intrusive process of biopsy into the muscle tissue. Though generally a small incision, this insult into a finely tuned and trained muscle can cause soreness and or pain, and may well temporarily impede muscle operation as the muscle tissue works to repair itself. The resulting pain, soreness and repair process may degrade performance during the event or training.

The analysis of a biopsy to determine glycogen store is also a time consuming process and by the time the results are known, the metabolism of the body and specifically the muscle may well have changed the level of muscle glycogen store up or down such that the biopsy determination can only be valued as a general gauge of the glycogen levels at a past time.

Moreover, the value of determining the glycogen store within a muscle may be entirely offset by the minor injury to the muscle entailed by the biopsy process if the injury results in degraded muscle performance. Adding to that possibility the latency in biopsy determination and the value of intrusive biopsy process is even further diminished.

As such, although such knowledge could be quite advantageous in helping to insure peak performance for an event or training, present evaluation of glycogen stores are generally educated guesswork based on past biopsy testing. Though helpful, guesswork is clearly not ideal especially for pro athletes and the sponsors of pro athletes who may invest significant sums of money, training time and sacrifice in the effort to be prepared for a specific event.

Knowledge of muscle glycogen stores is not strictly limited to athletes. Indeed, many people in many different settings could well be aided by knowing their own glycogen stores or the glycogen stores of those they work with and/or care for. For example the determination of glycogen stores in the muscles of a hospital patient could improve adjustments to his or care and nutrition. Likewise such knowledge could beneficially aid in the care of the elderly or infirm, and persons with certain medical conditions such as, but not limited to, diabetes might benefit from knowing glycogen muscle stores.

Hence there is a need for a method and system that is capable of providing non-invasive determination of glycogen stores, and to do so in near real time.

SUMMARY

This invention provides a method and system for non-invasive determination of glycogen stores.

In particular, and by way of example only, according to one embodiment of the present invention, provided is a non-invasive method of determining glycogen stores including: receiving an ultrasound scan of at least a portion of a target muscle; and evaluating at least a portion of the ultrasound scan to determine glycogen store within the target muscle.

In yet another embodiment, provided is a non-invasive method of determining glycogen stores including: providing an ultrasound device having a movable transducer, the transducer operable in a high frequency range; selecting a target muscle of a subject; adjusting the ultrasound device for a depth of scan appropriate for the selected target muscle; disposing the transducer proximate to the subject and perpendicular to the selected target muscle; scanning the selected target muscle by processing ultrasound reflection received by the transducer to provide at least a partial scan of the selected target muscle; selecting an area of the scan; and evaluating the selected area to determine glycogen store within the target muscle.

For another embodiment, provided is a method of endurance conditioning for a subject including: at a plurality of intervals during a period of endurance activity; disposing a transducer of an adjustable ultrasonic device proximate to the subject and perpendicular to a selected target muscle, the ultrasonic device adjusted for a depth of scan appropriate for the target muscle; scanning the selected target muscle by processing ultrasound reflection received by the transducer to provide at least a partial scan of the selected target muscle; selecting an area of the scan; evaluating the selected area to determine glycogen store within the target muscle; and adjusting the endurance activity to maintain the subject's glycogen store level at or above a pre-defined minimum glycogen store level.

Further, in yet another embodiment provided is a method for non-invasive determination of glycogen stores including: means for receiving an ultrasound scan of at least a portion of a target muscle; means for defining a plurality of areas within the ultrasound scan, each area having at least one attribute; means for quantifying each attribute as a value from a predetermined range of values; and means for processing the values to determine a glycogen store.

Still, in yet another embodiment, provided is a system for non-invasive determination of glycogen stores including: a glycogen evaluator structured and arranged to evaluate at least one selected portion of a scan of a selected target muscle to determine a glycogen store within the target muscle.

Further still, in yet another embodiment, provided is a system for non-invasive determination of glycogen stores including: an ultrasound device having a movable transducer, the transducer operable in a high frequency range, the ultrasound device having an adjustable depth of scan; a depth of scan selector structured and arranged to select the depth of scan based upon a selection of a target muscle type; and a glycogen evaluator structured and arranged to evaluate at least one selected area of a scan of a selected target muscle to determine a glycogen store within the target muscle.

And yet, for another embodiment, provided is a system for non-invasive determination of glycogen stores including: a processing unit; a memory storage device coupled to the processing unit; the processing unit being adapted to: receive an ultrasound scan of at least a portion of a target muscle of a subject; select an area of the scan; and evaluate the selected area to determine glycogen store within the target muscle.

Yet again, for another embodiment, provided is a system for non-invasive determination of glycogen stores including: A processor enabled device having at least one output device; an ultrasound device for coupling to the processor enabled device, the ultrasound device having a movable transducer, the transducer operable in a high frequency range, the ultrasound device having an adjustable depth of scan; a set of instructions to adapt the processor enabled device as a glycogen evaluator structured and arranged to evaluate at least one selected portion of a scan provided by the ultrasound device of a selected target muscle to determine a glycogen store within the target muscle and output the determined glycogen store.

Further still, in yet another embodiment, provided is a system for non-invasive determination of glycogen stores including: a processing unit; a memory storage device coupled to the processing unit; an ultrasound device having a movable transducer, the transducer operable in a high frequency range, the ultrasound device coupled to the processing unit; the processing unit being operative to: receive identification of a target muscle of a subject; adjust the ultrasound device for a depth of scan appropriate for the selected target muscle; scan the selected target muscle by processing ultrasound reflection received by the transducer to provide at least a partial cross sectional scan of the selected target muscle; select an area of the scan; and evaluate the selected area to determine glycogen store within the target muscle.

And further still, for yet another embodiment, provided is a non-transitory machine readable medium on which is stored a computer program for non-invasive determination of glycogen stores including, the computer program including instructions which when executed by a computer system perform the steps of: receiving an ultrasound scan of a target muscle; and evaluating at least a portion of the ultrasound scan to determine glycogen store within the target muscle.

And yet further, provided for another embodiment is a non-transitory machine readable medium on which is stored a computer program including instructions to adapt a computer system having a processor and an ultrasound device with a movable transducer to permit non-invasive determination of glycogen stores, the computer program including: an input routine operatively associated with an input device for permitting a user to enter a target muscle; a depth of scan routine for adjusting the ultrasound device for a depth of scan appropriate for the target muscle; an imaging routine for imaging the selected target muscle by processing ultrasound reflection receive by the transducer to provide at least a partial cross sectional scan of the selected target muscle; a define portion routine for selecting at least a portion of the scan; and an evaluating routine for evaluating the selected portion to determine glycogen store within the target muscle.

BRIEF DESCRIPTION OF THE DRAWINGS

At least one method and system for non-invasive determination of glycogen stores will be described, by way of example in the detailed description below with particular reference to the accompanying drawings in which like numerals refer to like elements, and:

FIG. 14 presents multiple charts illustrating the fatigue and the comparison of different target muscles in accordance with at least one embodiment;

FIGS. 16-18 are conceptual illustrations of alternative configurations for a system for non-invasive determination of glycogen stores in accordance with at least one embodiment.

DETAILED DESCRIPTION

Before proceeding with the detailed description, it is to be appreciated that the present teaching is by way of example only, not by limitation. The concepts herein are not limited to use or application with a specific system or method for non-invasive determination of glycogen stores. Thus although the instrumentalities described herein are for the convenience of explanation shown and described with respect to exemplary embodiments, it will be understood and appreciated that the principles herein may be applied equally in other types of systems and methods involving the non-invasive determination of glycogen stores.

Glycogen is a polysaccharide made up of glucose—a monosaccharide, or simple sugar and an important carbohydrate in biology. Indeed glycogen is a principle form of energy storage for an animal and therefore referred to as a "glycogen store." For ease of discussion and illustration, the embodiments of systems and methods as set forth herein discuss and describe non-invasive determination of glycogen stores, though the methods and systems may be applied for the detection of other monosaccharides or polysaccharides. Indeed, as used herein, the term glycogen is understood and appreciated to include other monosaccharides or polysaccharides within biological tissue as an energy reserve.

Figure 1:
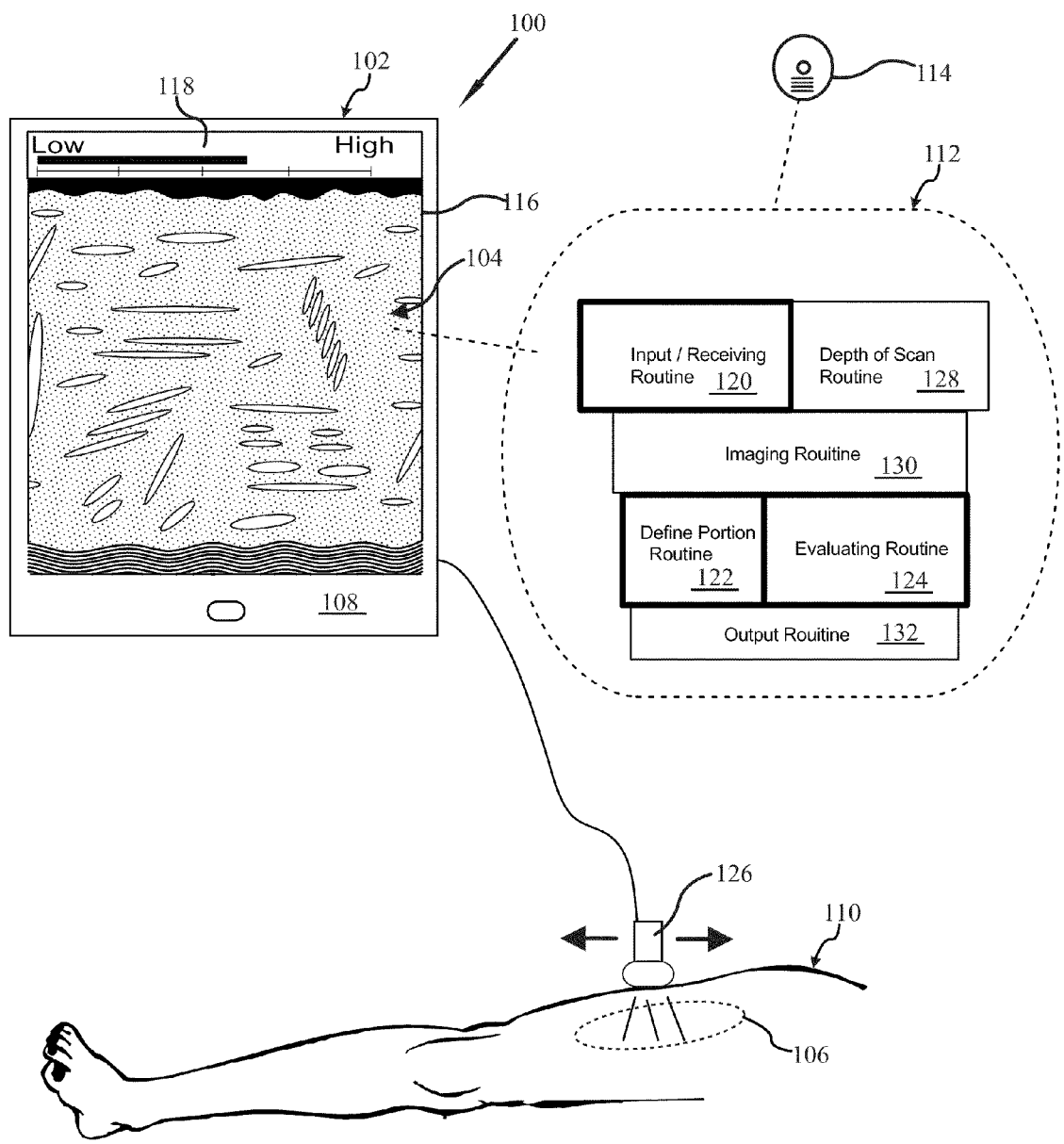
FIG. 1 illustrates a high level block diagram of a system for non-invasive determination of glycogen stores in accordance with at least one embodiment.

Turning to FIG. 1, presented is a high level block diagram of a system for non-invasive determination of glycogen stores (SNDGS) 100. Specifically, SNDS 100 is a glycogen evaluator 102 structured and arranged to evaluate at least one selected portion of a scan 104 of a selected target muscle 106 to determine a glycogen store within the target muscle 106.

As used herein the term "scan" is understood and appreciated for its normal meaning and as is expected in the medical profession—namely, "a. examination the body or an organ or part, or a biologically active material, by means of a scanning technique such as ultrasonography—an ultrasound-based diagnostic imaging technique used for visualizing subcutaneous body structures b. the image so obtained. Moreover the scan may be the collection of data from a scanner as well as an image representing that data, but it need not be an image in all cases.

Further the term "evaluate" and it's various derivatives is understood and appreciated for it's normal meaning, namely, "a. to determine or set the value or amount of appraise—b. to judge or determine the significance, worth or quality of; assess—c. to ascertain the numerical value of." However, with respect to the interpretation of scans, it is not uncommon to refer to the process of interpretation as analyzing, as in, "a. to separate into constituent parts or elements; determine the elements or essential features of—b. to examine critically, so as to bring out the essential elements or give the essence of—c. to examine carefully and in detail so as to identify causes, key factors, possible results, etc. . . . —d. to subject to mathematical, chemical, grammatical, etc., analysis." Moreover, as used herein, "evaluate" and it's derivative forms are understood and appreciated to encompass the aspects of "analysis" as may be appropriate for a given situation.

In at least one embodiment, SNDGS 100 has a processor-enabled device such as computer 108. Computer 108 is adapted to receive the scan 104 of a target muscle 106 of a subject 110, FIG. 1 showing only a portion of the subject's right leg.

With respect to FIG. 1, the conceptual illustration suggests the subject 110 is a human being. Indeed, embodiments of SNDGS 100 are indeed directed towards the non-invasive detection and analysis of glycogen stores within human beings, such as for example, elite athletes such as professional cyclists, triathletes, speed skaters, swimmers, down hill and slalom skiers, football players, lacrosse players, soccer players, and or other such endurance athletes or individuals such as military personnel, where sustained performance over an extended period of time is a significant factor in the person's training and conditioning. It should also be understood that varying embodiments of SNDGS 100 might also be applied to non-human subjects, such as racehorses or other animals.

With respect to FIG. 1, SNDGS 100 is at least in part conceptually illustrated in the context of an embodiment for a computer program 112. Such a computer program 112 can be provided upon a non-transitory computer readable media, such as an optical disc 114 or RAM drive that can be provided to a computer 108 to be adapted as SNDGS 100. As is further shown and described in connection with FIG. 16, in alternative embodiments the computer program 112 can be provided to a computer serving at least as part of an application providing platform, such as but not limited to the Apple App Store, that computer in turn operable to provide the computer program to a computer 108 to be adapted as SNDGS 100.

As will be discussed further below, SNDGS 100 may be employed upon a computer 108 having typical components such as a processor, memory, storage devices and input and output devices. During operation, the SNDGS 100 may be maintained in active memory for enhanced speed and efficiency. In addition, SNDGS 100 may also be operated within a computer network and may utilize distributed resources.

In at least one embodiment, the SNDGS 100 system is provided as a dedicated system to provide non-invasive determination of glycogen stores. In at least one alternative embodiment, the SNDGS 100 system is achieved by adapting an existing computer 108 such as a smart phone (such as an iPhone® or Android®) or tablet computer (such as an iPad®) which is portable.

With respect to FIG. 1, SNDGS 100 has been conceptually illustrated as a tablet computer 108, having a display 116 operable to display a visual representation of the scan 104. The display 116 also is shown to provide an indicator 118 to inform an operator of the determined glycogen store.

For at least one embodiment, the software may be described as including an input/receiving routine 120, a define portion routine 122, and an evaluating routine 124. As is set forth and described below, the elements of SNDGS 100 may be summarized or at least one embodiment as follows.

The input/receiving routine 120 is operable to receive the scan 104, such as a Digital Imaging and Communications in Medicine (DICOM) data file, and may also receive other information such as the subjects name, location, current state of exertion, etc. . . . The define portion routine 122 is operable to define a plurality of areas within the scan 104 of the target muscle 106. The evaluating routine 124 is operable to evaluate at least one attribute for each of the plurality of areas to determine the glycogen store within the target muscle.

In addition to the three core routines, input/receiving routine 120, define area routine 122 and the evaluating routine 124 shown with heavy boarders, in at least one alternative embodiment, SNDGS 100 further includes an ultrasound device having a movable transducer 126 operable in a high frequency range and has a an adjustable depth of scan. More specifically, the high frequency range is between about 5 to 20 megahertz. In addition the depth of scan is between about 1 centimeter and about 7 centimeters. For at least one embodiment, the ultrasound transducer 126 is an existing commercially available and FDA approved ultrasound transducer 126 incorporated as part of SNDGS 100 without departing from the scope of FDA approval for the operation of the ultrasound transducer device.

For at least one embodiment of SNDGS 100, the computer program 112 may additionally include a depth of scan routine 128, an imaging routine 130, and optionally an output routine 132. Moreover, the depth of scan selector routine 128 is operable to adjust the ultrasound device, e.g., ultrasound transducer 126, for a depth of scan appropriate for the target muscle 106. In at least one embodiment, the proper depth of scan is set based on the selection of a target 106 muscle as indicated by an operator of SNDGS 100.

The imaging routine 130 is operable to direct the movable transducer 126 to scan the selected target muscle 106 by processing ultrasound reflection received by the transducer to provide at least a partial ultrasound scan of the selected target muscle. In at least one embodiment, the imaging routine 130 is structured and arranged to operate with a third party ultrasound imaging software provided to the computer 108.

For at least one embodiment, the optional output routine 132 is operable to output the scan of the target muscle 106 to a storage device, or database. This output routine may also be configured to provide an audible, visual or tactile output to inform the operator of SNGDS 100 of the determined glycogen store for the target muscle 106.

With respect to FIG. 1, it is understood and appreciated that the elements, e.g., input routine 120, define area routine 122, evaluating routine 124, depth of scan routine 128, imaging routine 130, output routine 132, ultrasound transducer 126 and computer 108 are in at least one embodiment located within a single device. In at least one alternative embodiment, these elements may be distributed over a plurality of interconnected devices. Further, although each of these elements has been shown conceptually as an element, it is understood and appreciated that in varying embodiments, each element may be further subdivided and/or integrated with one or more other elements.

Figure 2:
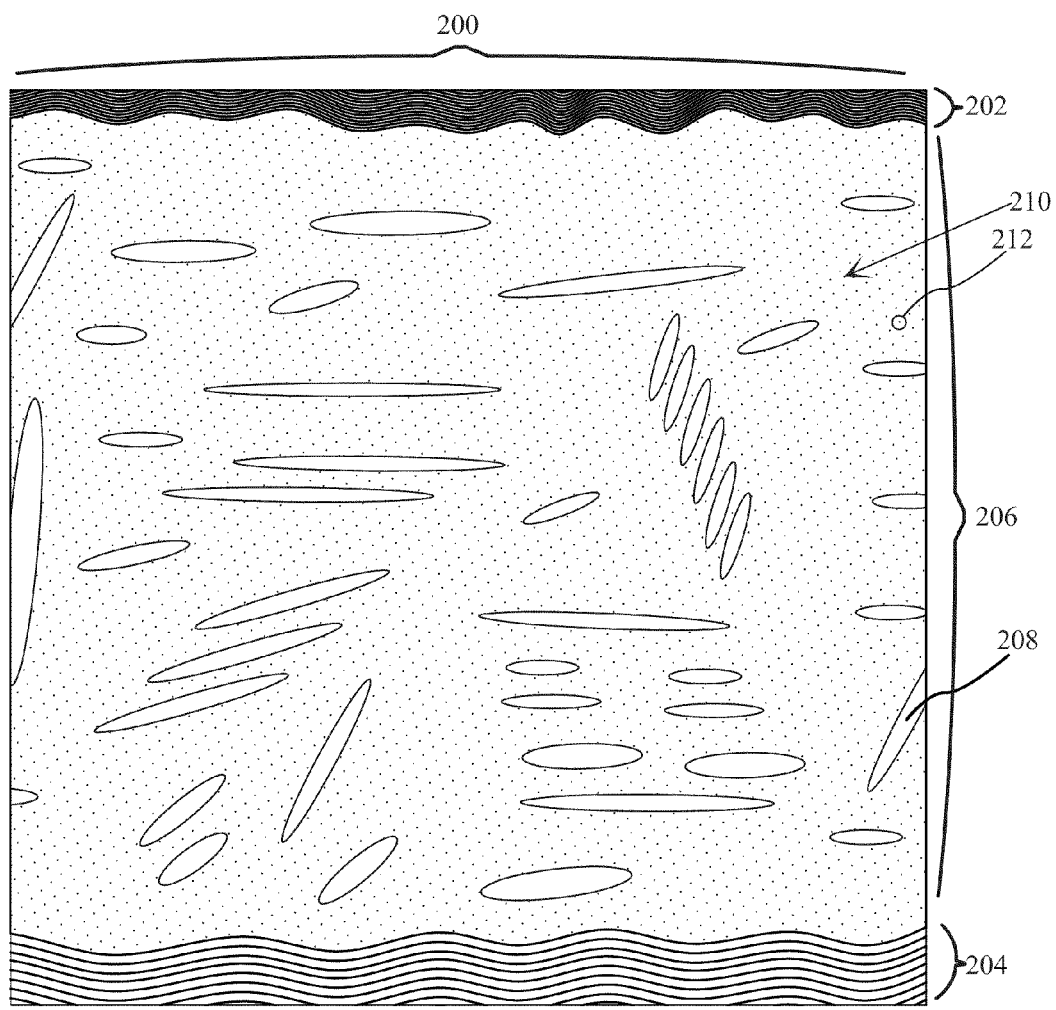
FIG. 2 is a conceptual illustration of an ultrasound scan of a target muscle in accordance with at least one embodiment.
Figure 3:
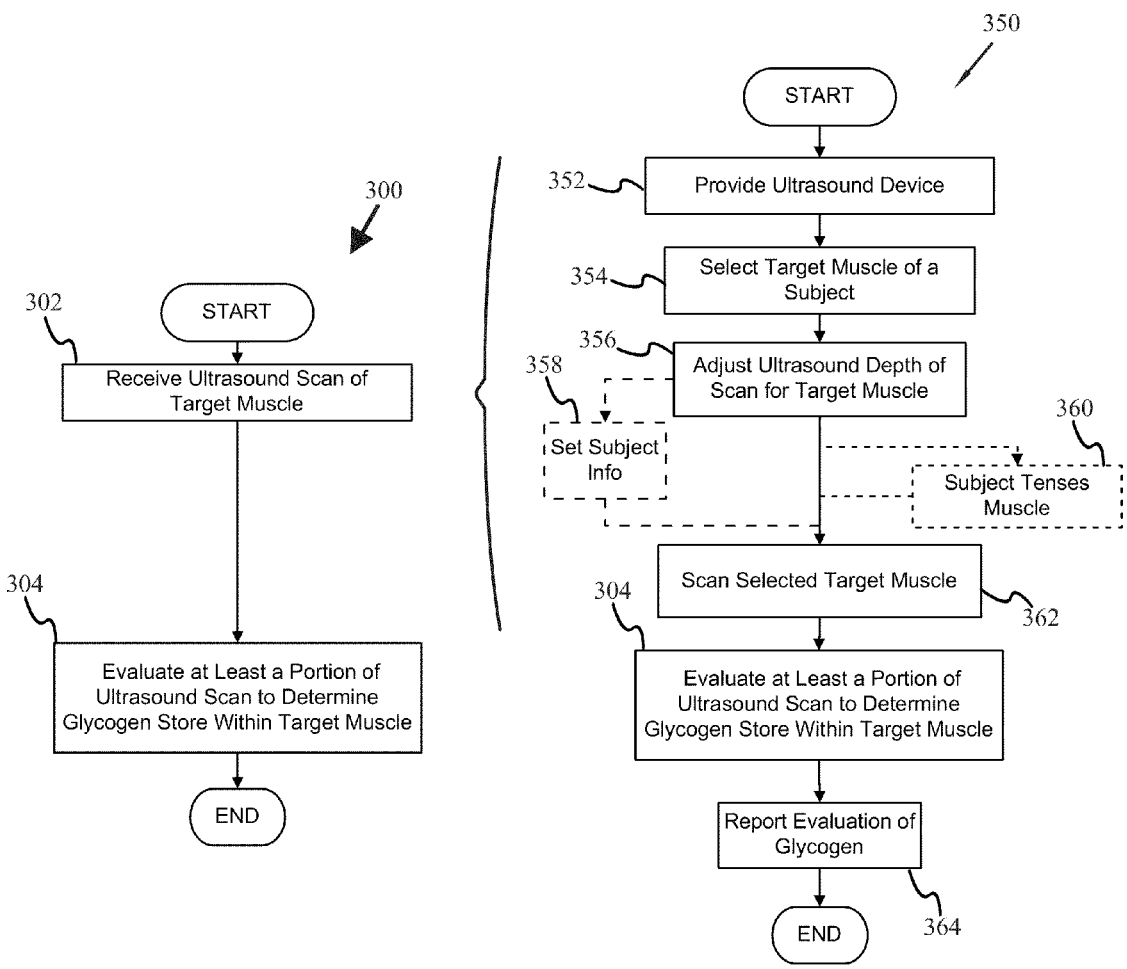
FIG. 3 illustrates a high level flow diagram for a method of non-invasive determination of glycogen stores in accordance with at least one embodiment.

FIGS. 2 and 3 in connection with FIGS. 1 and 3-13 provide a high level flow diagram with conceptual illustrations depicting a method 300 for non-invasive determination of glycogen stores in accordance with at least one embodiment. It will be appreciated that the described method need not be performed in the order in which it is herein described, but that this description is merely exemplary of one method of non-invasive determination of glycogen stores.

As is shown in FIG. 2, the scan 200 may capture a portion of the surface tissue 202, such as the skin and underlying fat and tissue layers. The scan 200 may also capture a portion of the deep tissue 206, bone, tendon, organ, or other tissue that is below the target muscle 106. Primarily, the scan 200 captures at least a portion of the target muscle 106, more specifically the target muscle tissue 206. Running throughout the muscle tissue 206 are various non-muscle tissues 208, such as but not limited to connective tissues, tendon tissues, and vascular tissues.

As the scan 200 presents at least a cross section of the muscle tissue 206, it is understood and appreciated that non-muscle tissue 208 that is truly within, connected to, or in contact with the muscle tissue 206 may appear as part of, or otherwise within the muscle tissue 206. For the purposes of non-invasive glycogen store determination as set forth herein, non-muscle tissues 208 that appear within the scan 200 of the muscle tissue 206 may be considered to be part of the muscle tissue 206.

Glycogen stores 210 within the muscle tissue 206 are shown in FIG. 2 and in the accompanying figures as dots, with dot 212 being exemplary. For conceptual illustration and ease of discussion, the larger the glycogen store 210 the larger the dot 212. It is to be understood and appreciated that muscle glycogen stores 210 are naturally occurring within the muscle tissue 206. Moreover, the methods and systems disclosed herein for non-invasive determination of glycogen stores 210 within a target muscle 106 are advantageously distinct and directed to naturally occurring glycogen stores 210, not injected glycogen as has been used to highlight internal structures and or features.

With respect to the development of glycogen stores 210, carbohydrates are arguably the most important source of energy for animals, and more specifically mammals including human beings. Once eaten, carbohydrates are broken down into simple sugars such as glucose, fructose and galactose that are absorbed by cells and used for energy. Glucose that is absorbed by a muscle cell but not immediately needed is stored as glycogen, e.g., the glycogen store 210. Muscle conditioning and training can increase the amount of glycogen stores 210. Whether through activity or simply the passage of time between eating or otherwise receiving carbohydrates or glucose, the glycogen store 210 within muscles will be depleted.

With respect to the ultrasound scan 200, glycogen stores can be detected as one or more attributes within the scan 200. More specifically, in many cases the scan 200 is rendered to a user of an ultrasound scanning system as an image. The attributes of the image correspond to sonogram reflection. More specifically, in at least one embodiment the scan 200 is represented as an image with attributes represented as luminance, color, contrast and or combinations thereof.

Further, although the accompanying FIGS. 1, and 2, 5-11 and 13 depict the scan 104 as an image, the interpretation of the scan 104 as an image has been chosen to facilitate ease of discussion and illustration. Indeed it is to be understood and appreciated that the in varying embodiments of systems and methods for non-invasive glycogen detection, attributes of the scan 104 may be interpreted without rendering an image to a user. Indeed, as is further discussed below other visual, audible or tactile notifications can be used to signify the determined glycogen store with or without displaying an image of the scan to a user.

Further, although the illustrations and discussion provided herein for exemplary purposes generally appear to be 2D (two dimensional) images, the system and methods are equally applicable multi-axis ultrasound imaging techniques, such as for example 3D ultrasound.

FIG. 3 in connection with FIG. 1 provides a high level flow diagram with conceptual illustrations depicting a method 300 for non-invasive determination of glycogen stores within a target muscle 106. It will be appreciated that the described method, as well as all other subsequent methods and refinements to the disclosed methods need not be performed in the order in which they are herein described, but that the descriptions are merely exemplary of a method or methods that could be performed for non-invasive glycogen determination.

More specifically, as in FIG. 3, for at least one embodiment, method 300 commences with receiving an ultrasound scan 104 of at least a portion of a target muscle 106, block 302. With the scan 104 received, at least a portion of the ultrasound scan 104 is evaluated to determine the glycogen stores 210 within the target muscle 106, block 304.

For application of method 300, an embodiment of SNDGS 100 need not have, or otherwise be coupled to, an ultrasound transducer 126. Method 300 may also be performed by SNDGS 100 when a user desires to review historical data of target muscle scans, such as for example to revisit past histories of evaluation to perceive changes in development and potential adjustments to a subject's training methods.

Of course for real time and non-invasive determination of glycogen stores, in varying embodiments SNDGS 100 may indeed include an ultrasound transducer 126 as described above. As such, method 300 may be augmented as method 350, the augmentation as illustrated pertaining to at least one method of providing the received ultrasound scan 104.

More specifically, for augmented method 350, an ultrasound transducer 126 is provided as part of SNDGS 100, block 352. A target muscle, e.g. target muscle 106, is selected, block 354. As noted, the ultrasound transducer has an adjustable depth for scanning, such as a selection between about 0.5 and 10 centimeters. The ultrasound transducer 126 is adjusted to provide a depth of scan appropriate for the selected target muscle, block 356.

In at least one embodiment, the depth of scan is adjusted manually, such as to about 3.5 centimeters for the rectus femoris muscle. In an alternative embodiment, the depth of scan is automatically selected by an operator selecting a muscle, e.g., rectus femoris, vastus lateralis, or biceps. In addition, in varying embodiment, the auto-determined and set depth may also be adjustable by the operator so as to permit adjustment for various body types.

In at least one embodiment additional and optional information about the subject is recorded, as indicated by dotted block 358. This optional information may include, but is not limited to, details such as the subjects name, age, gender, time of day, status of subject—at rest/at VOT Max, after eating, or other such information desired to be recorded and displayed in connection with the scanned image of the target muscle.

Moreover, to summarize for at least one embodiment, the augmented method 350 includes providing an ultrasound device having a movable transducer, the transducer operable in a high frequency range, selecting a target muscle 106 of a subject 110 and adjusting the ultrasound device for a depth of scan appropriate for the selected target muscle 106.

As the ultrasound transducer 126 operates by providing a high frequency signal that is directed into tissue and detecting reflections returned by encountered elements, it is understood and appreciated that the transducer should be aligned generally perpendicular to the selected target muscle. Of course, if a transducer having an alignment configuration that is other than perpendicular is employed the specific alignment as intended for the transducer should be used.

Testing has determined it is substantially immaterial as to whether the ultrasound transducer 126 is positioned along the longitudinal or latitudinal axis of the muscle, or somewhere there between. However for general alignment purposes and ease of operation, in general the operator of the system will select ultrasound transducer 126 alignment matching to either the longitudinal or latitudinal axis of the target muscle 106.

Application of the ultrasound transducer 126 against the subjects skin can be a practiced skill, for if too much pressure is applied the transducer may inadvertently compress the muscle tissue and thereby hamper the quality of the scan and the resulting evaluation of glycogen stores. However, an easy solution presents itself that substantially minimizes the risk of transducer related compression of the tissue.

As shown by optional dotted block 360, the subject can simply tense his or her target muscle 106. More specifically, if the subject acts to tense the selected target muscle 106, the natural action of the muscle contraction causes the muscle to swell and thereby resist compression. The contracted and thereby enlarged target muscle 106 may also be advantageous in providing an even clearer cross sectional scan then may be obtained with a relaxed muscle.

In short, while the quality of the scan for the tensed or un-tensed target muscle 106 may be the same for an operator skilled in how much pressure to apply, for the novice, as well as the skilled operator, tensing the target muscle 106 does not hamper the determination of glycogen stores 210 and may help insure greater consistency of scans in a wide variety of locations and settings. Indeed, for at least one embodiment, when the method of scanning a target muscle 106 is performed, the subject will tense his or her target muscle 106 as a normal and expected part of the scanning process.

Moreover, to achieve the scan of the target muscle 106, the ultrasound transducer 126 is disposed proximate to the target muscle and as the ultrasound transducer 126 is activated the target muscle 106 is scanned, block 362. In at least one embodiment the ultrasound transducer 126 is placed in direct contact with the subject's skin. In at least one alternative embodiment, a protective cover, shield or even the subject's clothing is disposed between the ultrasound transducer 126 and the target muscle 106.

In other words, to summarize for at least one embodiment, the augmented method 350 continues with disposing the transducer proximate to the subject 110 and perpendicular to the selected target muscle 106, and then imaging the selected target muscle 106 by processing ultrasound reflection received by the transducer to provide at least a partial scan of the selected target muscle 106. Many ultrasound transducers provide images as cross sections of the tissues and structures whereas others may provide 3-D views. For consistency in analysis, in at least one embodiment the operator of SNDGS 100 adopts a convention to scan a target muscle along its long axis or short axis. For the majority of leg and arm muscles the long axis is generally parallel to bone structure and the short axis is generally perpendicular to bone structure. Indeed in some embodiments, scans with SNDGS 100 may be performed substantially contemporaneously along both the long and short axis of a target muscle 106 for enhanced comparison and analysis.

Method 350 then continues with the evaluation of the scan as discussed above with respect to block 304. For at least one embodiment, it is understood and appreciated that the evaluation of the scan 104 is performed about contemporaneously with the scanning of the target muscle 106.

The determined glycogen store 210 is then reported to the operator, block 364. The determined glycogen store may also be recorded for use in plotting the changes in a subjects glycogen store over time, and or in response to various different points of exercise and conditioning as well as different periods of exertion such as in endurance activities.

In at least one embodiment, the evaluation of the scan to determine the glycogen store with the target muscle 106, is based on the visual experience of the operator performing the method 300, and or enhanced method 350 with respect to a visual image provided by the scan. More specifically an experienced individual can provided qualitative analysis of the glycogen store by visually determining an are of the cross section image to focus on and then evaluating that selected portion based on historical experience.

Methods 300/350 and or SNDGS 100 can advantageously be utilized by a greater audience of benefitted parties where the evaluation is performed as an automated, or at least partially automated evaluation process.

Figure 4:
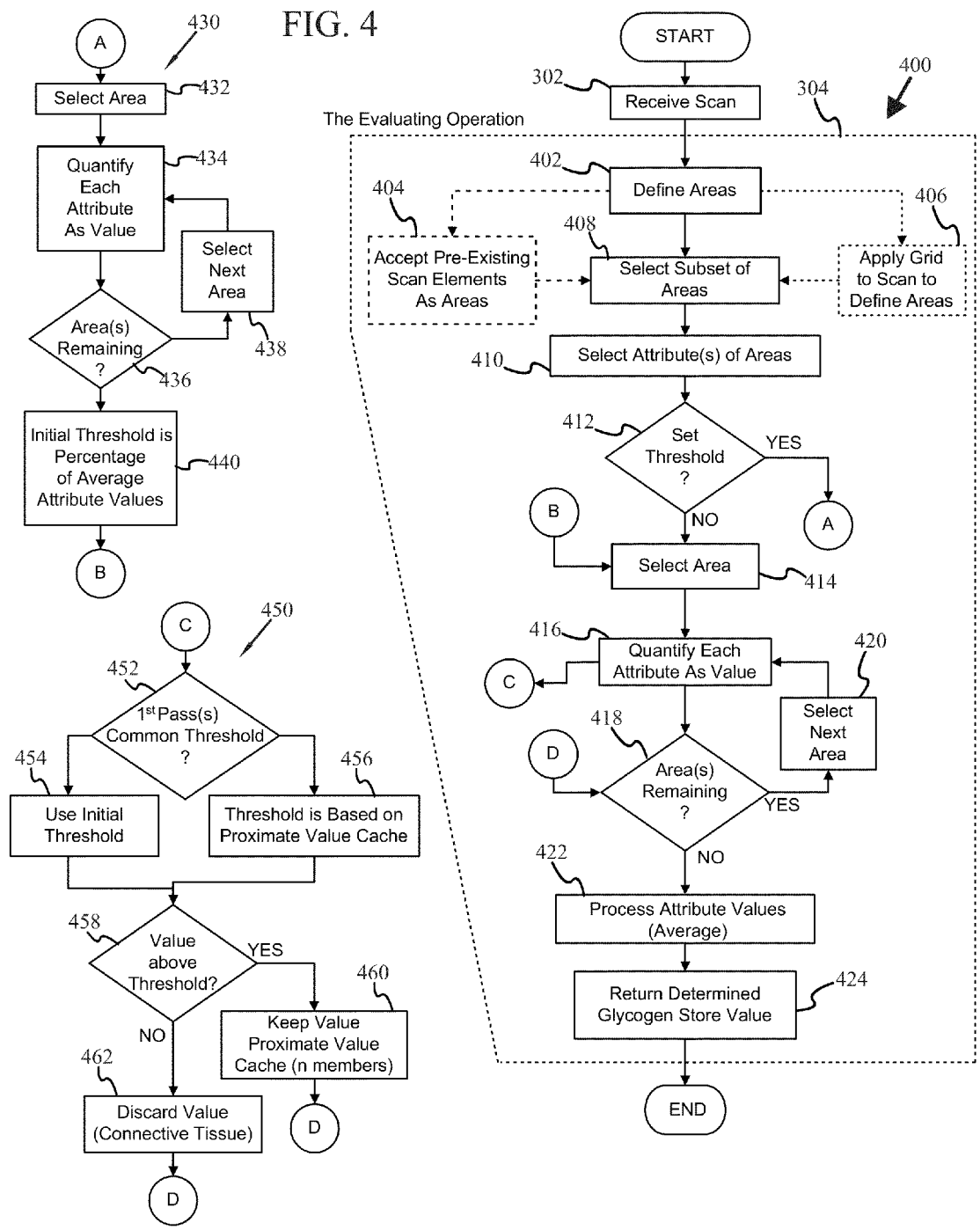
FIG. 4 is a refined flow diagram of the evaluating operation for non-invasive determination of glycogen stores in accordance with at least one embodiment.

FIG. 4 in connection with FIGS. 5-13 provides a high level flow diagram with conceptual illustrations to further refine at least one embodiment of method 400 for evaluating at least a portion of the ultrasound scan to determine glycogen stores 210 within the target muscle 106. Again it is appreciated that the described method need not be performed in the order in which it is herein described, but that this description is merely exemplary of one method for non-invasive determination of glycogen stores within a target muscle.

Figure 5:
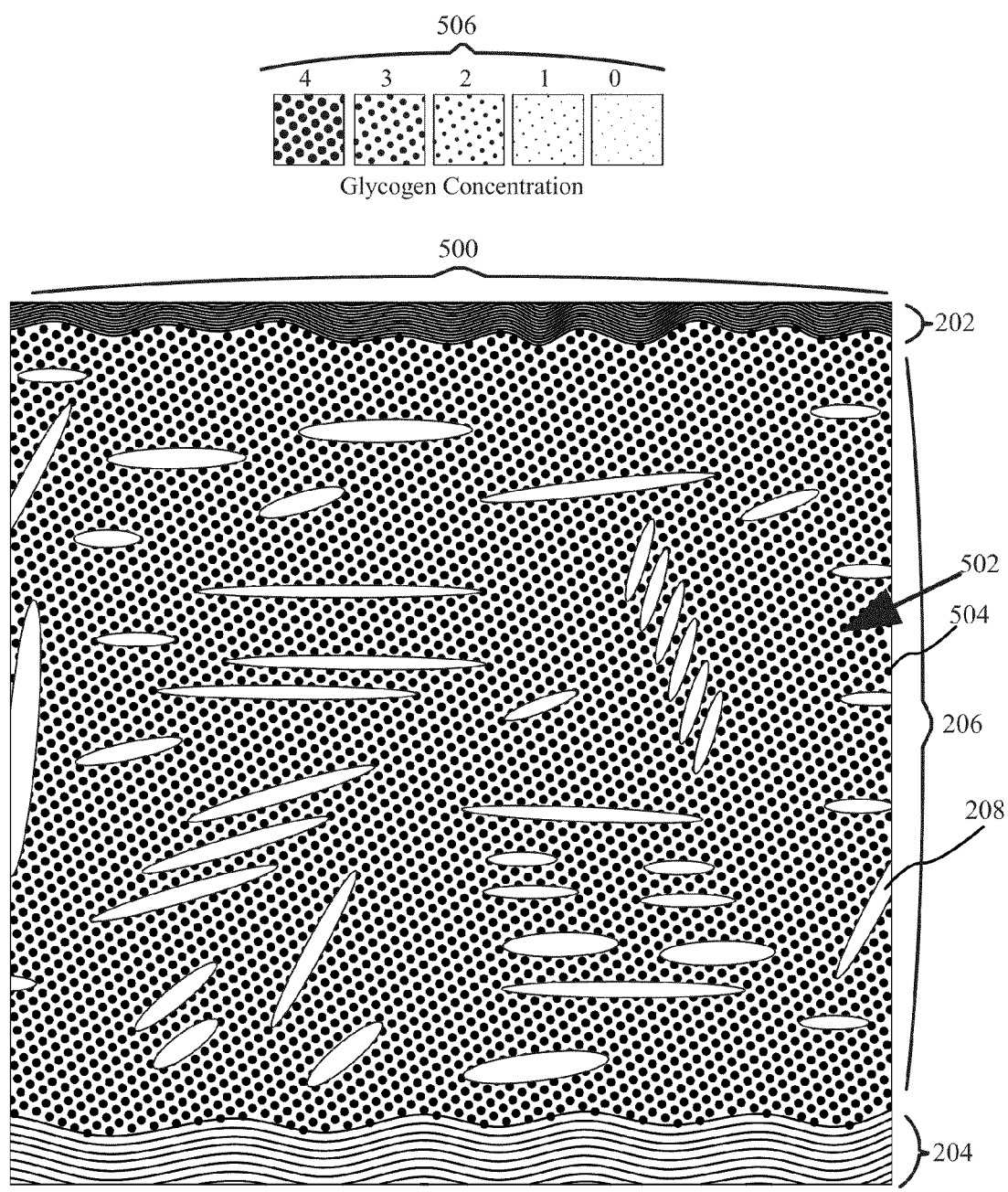
FIG. 5 is a conceptual illustration of an ultrasound scan of a target muscle at a first time interval in accordance with at least one embodiment.

More specifically, as FIG. 4 expands on FIG. 3, initially a scan of a target muscle 106 is received, block 302. An exemplary scan such as scan 500 is shown in FIG. 5. As previously shown and described with respect to FIG. 2, scan 500 includes skin and or other surface tissue 202, deep tissue 204 and target muscle tissue 206, with elements of non-muscle tissue 208. The glycogen store 502 within scan 500 is conceptually shown to be high by the use of large dots 504 providing a substantially dark appearance to the scanned portion of the target muscle tissue 206.

A pre-established glycogen concentration scale 506 is also shown. The pre-establishment of the glycogen concentration scale 506 aids in the effective identification of attributes that are correlated to the glycogen store, e.g., color, contrast, darkness, luminance and or combinations thereof.

In at least one embodiment a precise reference of glycogen store values as a gradient scale is established by contemporaneously taking an ultrasound cross sectional image and a biopsy of the same target muscle at systematic stages of exercise to exhaust the glycogen stores, and or carbohydrate replenishment to re-establish the glycogen stores. The empirical data from a plurality of subject can establish an advantageous reference that is applicable to many different subjects.

It is also understood and appreciated that in at least one embodiment, an even more precise predetermined reference can be established for a specific subject by the contemporaneous imaging and biopsy process upon that subject. Alternatively, a general glycogen concentration scale 506 as established from one or more other subjects may be refined for a specific subject based on repeated application of the methods 300/350/400 and or SNDGS 100.

As shown the glycogen concentration scale 506 covers a range. For ease of illustration and discussion the exemplary range as shown is from 4 to 0. An actual range as applied in methods 300/350/400 and or in SNDGS 100 may be greater or smaller. For purposes of the exemplary embodiments and description thereof, the valuation of 4 is appreciated to be a glycogen store of about 100% (e.g., the target muscle is at its maximum glycogen store) and a valuation of 0 is appreciated to be a glycogen store of about 0% (e.g., the target muscle has depleted its glycogen store).

Moreover, as is further discussed below, the glycogen scale—whether pre-established for a specific subject, or based more generally upon data from a plurality of test subjects permits a user of SNDGS 100 to advantageously and non-invasively determine the glycogen store within a target muscle 106. It should also be appreciated that this determination may be made upon a subject in nearly any setting or environment. In other words SNDGS 100 may be used and the glycogen store determined in a real time setting where the subject either is about to engage in an endurance activity or is engaged in training for endurance activity.

To evaluate the glycogen store 502 within the muscle tissue 206, method 400 proceeds by defining a plurality of regions within the scan 500. In at least one embodiment the plurality of regions or parts are a plurality of areas, block 402. These regions or areas can be defined in a variety of ways.

For at least one embodiment, pre-existing scan elements are accepted as the scan areas, as indicated by optional dotted block 404. In varying embodiments these pre-existing scan elements are one or more scan pixels. Where the scan is treated as an image, scan pixels may correlate directly with image pixels and image pixels may be used as the pre-existing elements.

Figure 6:
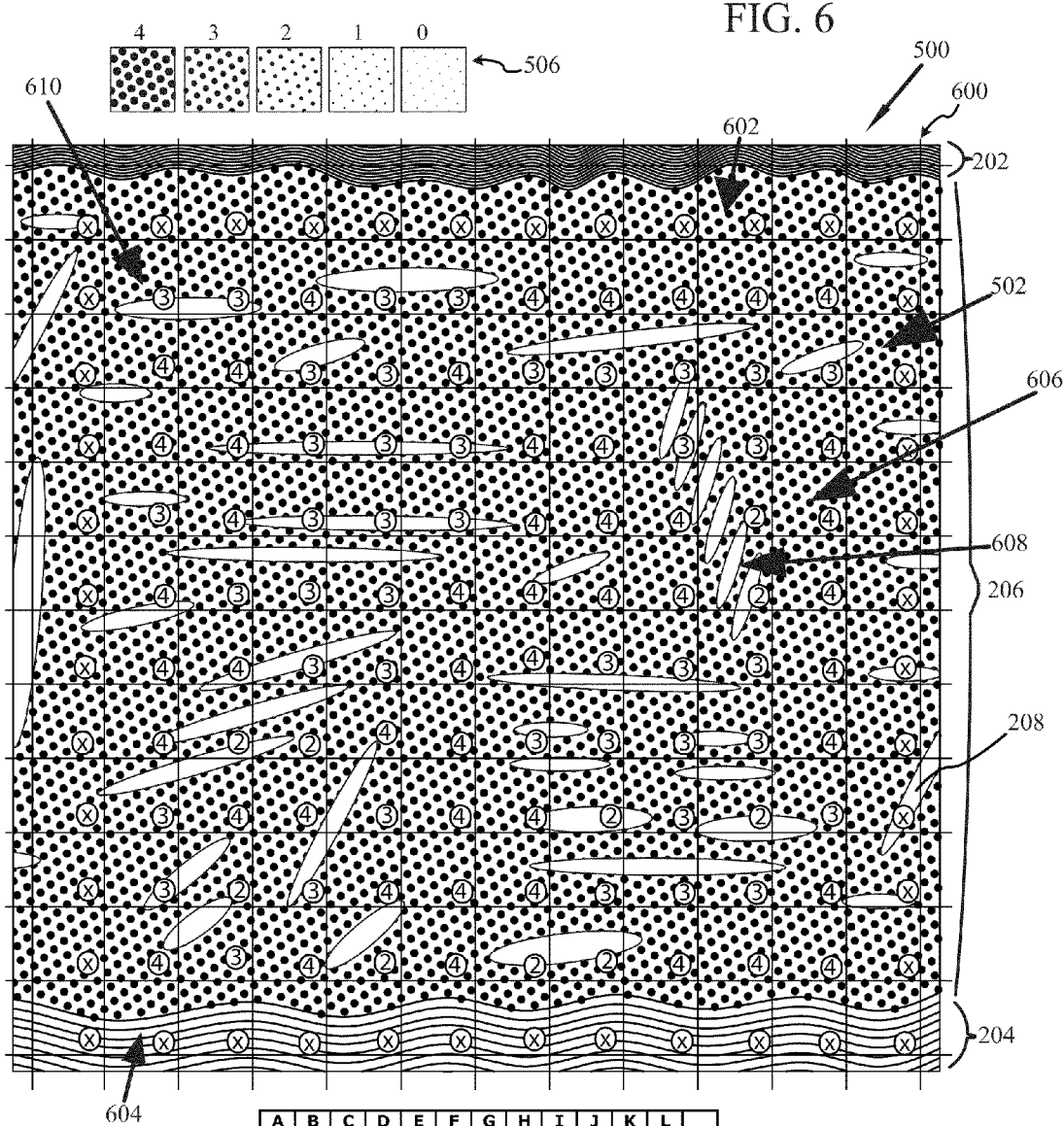
FIG. 6 is a conceptual illustration of the ultrasound scan of FIG. 5 with a grid and area attribute valuations in accordance with at least one embodiment.

In an alternative embodiment, as shown in FIG. 6 the plurality of areas are defined by applying a grid 600 to the scan 500. For ease of illustration and discussion the scan 500 is shown as an image, but it is understood and appreciated that the evaluating operation may be performed by working with the scan 500 as an image or as simply data, neither of which is actually displayed to an operator.

To summarize, for at least one embodiment the evaluating of at least a portion of the ultrasound scan 500 includes defining a plurality of areas within the ultrasound scan 500, each area having at least one attribute.

As shown in FIG. 6 the grid 600 is conceptually illustrated as a 12×12 grid for ease of illustration, thereby providing one hundred and forty four areas 602. In varying embodiments a larger or smaller grid may be applied. As is further shown in FIG. 6 a subset of the areas 602 is then selected, block 408.

Moreover, it is not unusual for the sides of the scan to be somewhat unclear, and as shown in FIGS. 5 and 6 there is both surface tissue 202 and deep tissue 204 partially captured in the scan 500 in addition to the desired muscle tissue 206. These undesired areas, of which area 604 is exemplary, are therefore removed from further consideration as indicated by the presence of a circled-X in each undesired area.

If not previously set, at least one attribute of the areas 602 is then selected, such as color, luminance, darkness, contrast or other identifiable attribute and/or combinations thereof, block 410. Moreover, the ultrasound scan as a data file may well contain information that although highly beneficial and adaptable for the determination of glycogen stores is blurred or otherwise rendered less clear when the scan is rendered as an actual image to an operator. As such, it is understood and appreciated that non-visual attributes as well as visual attributes may also be utilized alone or in combination with one another in varying embodiments for the non-invasive determination of glycogen stores.

In at least one embodiment the attribute of comparison is hypoechoic appearance as opposed to Hyperechoic (also known as echogenic) appearance. More simply stated the evaluation is a comparison of the attributes within an area 602 to a scale of black to white. Again for illustrative purposes the attribute selected in the present example is dot size.

With respect to FIGS. 5 and 6, it is clear that the presence of non-muscle tissues 208 affect the apparent concentrations of glycogen stores, e.g., the dots, in some areas but not others. More specifically, exemplary area 606 is shown to have no non-muscle tissue 208 while exemplary area 608 has a substantial non-muscle tissue 208 component. In at least one embodiment, the identification and discounting of non-muscle tissue 208 is achieved. Moreover this advantageous identification and discounting can be achieved through the use of a threshold in area evaluation.

To simplify the initial walk through of method 400, initially the threshold will not be set, decision 412.

Method 400 therefore proceeds to select an area 610 that has not been removed from further consideration, block 414. The attribute of this area 610 is then quantified as a value, block 416. More specifically the attribute of the selected area 610 is compared to the glycogen concentration scale 506 and an appropriate value assigned to the area 610, shown as the value within the circle—a 3 in the case of area 610. For example exemplary area 606 is quantified as a 4 whereas exemplary area 608 is quantified as a 2.

Method 400 proceeds with a query as to whether there are remaining areas to be quantified, decision 418. If additional areas remain, a new area is selected, block 420 and the attribute(s) are again quantified, block 416. In at least one embodiment, the selection of the next element is based on a sweep operation, e.g., starting at the far left and moving across an entire row before moving then to the next row and starting again at the far left. This sweep methodology can of course be adapted to move from right to left and from top to bottom or bottom to top of columns. The sweep method of selection is merely exemplary and is not a limitation precluding alternative selection schemes. Indeed, in at least one embodiment utilizing multiple processors and/or processes the selection and evaluation of all areas may be performed substantially simultaneously.

To summarize again, the evaluating of at least a portion of the ultrasound scan 500 includes, for at least a subset of defined areas 602, quantifying each attribute as a value from a predetermined range of values.

With the attributes of all areas now quantified as values, the values are processed to determine a glycogen store for the target muscle 106 as scanned and represented by scan 500, block 422. Collectively, the values assigned to the attributes represent a data set. For at least one embodiment the processing of the values is an action to determine the central tendency of the data set.

Determining the central tendency of a set identifies the "center" of the distribution of values within the sets. There are three general types of estimates of central tendency and they are respectively, the mean, the median and the mode. To compute the mean, it is generally understood to take the sum of the values and divide by the count. This is commonly known as averaging. The median is the score found at the middle of the set of values, which is to say that there are as many cases with a larger value as there are cases with a smaller value. The mode is the most frequently occurring value in the set, e.g., the value occurring with the greatest frequency.

Other options for statistical measures of the values by processing them may also be performed such as standard deviation and range. Even for an average, there are three common choices—arithmetic mean (sum divided by count), the geometric mean (n member are multiplied together and then taking the nth root), and the harmonic mean (for a set s of numbers $a_1, a_2, \ldots a_n$ it is the reciprocal of the arithmetic mean of the reciprocals of a/s).

For various embodiments, processing of the values may also include the application of a constant value or other formula. In general and for the varying embodiments employing different forms of processing for the quantified values, the intent is to achieve a value that is representative of the glycogen store within the target muscle as represented by the scan of the muscle tissue.

In at least one embodiment the processing of the values is averaging the values, e.g., an arithmetic mean. Moreover, in FIG. 6 a table 612 is shown with columns A~L and rows 1~12 correlating to the defined areas 602 of scan 500. The quantified values of the selected attribute for each area are shown and the overall average is shown to be 3.38. Based on the glycogen concentration scale 506 the determined value of 3.38 at time $X_1$ is understood and appreciated to be a high glycogen store value.

The determined glycogen store value is then returned, block 424. In varying embodiments the determined value may be returned to the operator as the quantified value, or as a representation of the value—such as but not limited to color, sound, vibration, or combinations thereof as well as varying intensity thereof.

Use of SNDGS 100 and or method 300/350/400 has many practical applications, not the least of which is to assist in athletic and/or endurance training. Another application is for rehabilitation wherein it is highly desirable to quantify how the muscle tissues are repairing and/or rebuilding. Further still, another application would potentially benefit incapacitated subjects, such as hospital patients, the infirm, the elderly or other persons who may for one reason or another have difficulty communicating. As such, for at least one embodiment, the method and or use of SNDGS 100 may be repeated over time upon the same target muscle 106.

Figure 7:
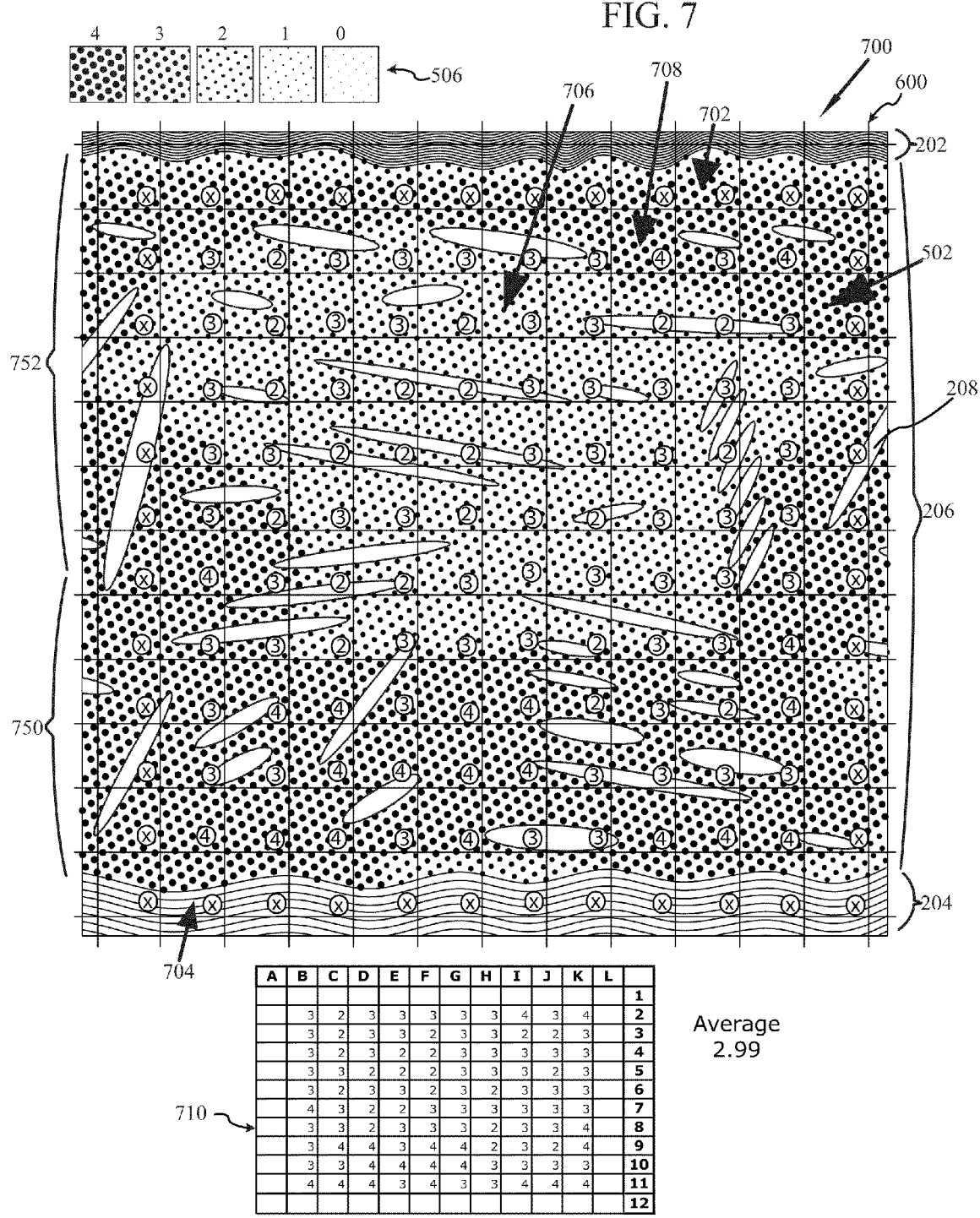
FIG. 7 is a conceptual illustration of an ultrasound scan of a target muscle at a second time interval with a grid and area attribute valuations in accordance with at least one embodiment.
Figure 8:
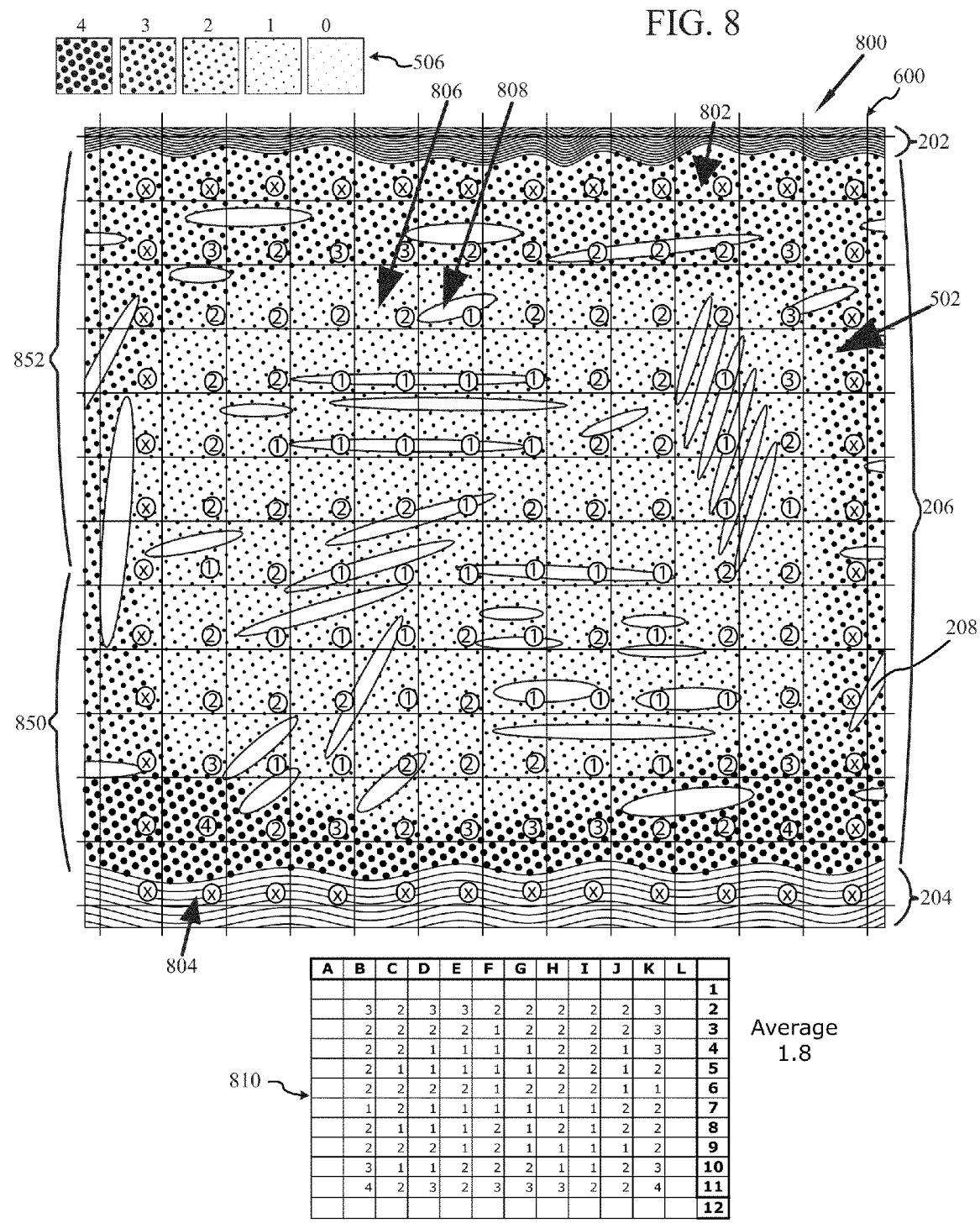
FIG. 8 is a conceptual illustration of an ultrasound scan of a target muscle at a third interval a grid and area attribute valuations in accordance with at least one embodiment.
Figure 9:
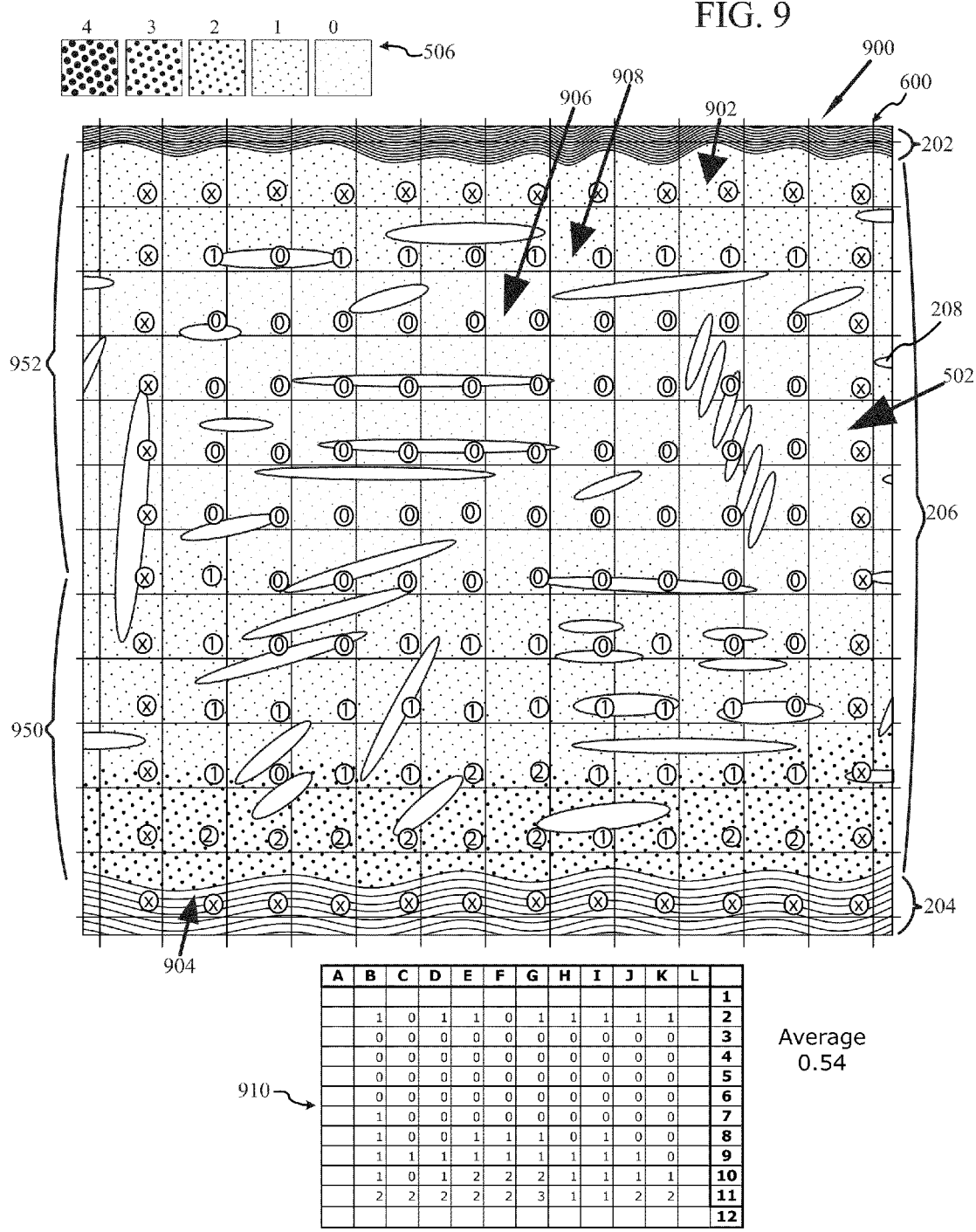
FIG. 9 is a conceptual illustration of an ultrasound scan of a target muscle at a fourth interval a grid and area attribute valuations in accordance with at least one embodiment.

FIGS. 7-9 conceptually illustrate repeated testing upon the same target muscle at time intervals of X during a subject's workout. As such, not only do FIGS. 6-9 cooperatively work to demonstrate how the method and or use of SNDGS 100 can advantageously assist in establishing an understanding of a subject's glycogen stores over time during exercise, each of FIGS. 6-9 when compared with the other FIGS. 6-9 also can help aid in understanding how the method and or use of SNDGS 100 can advantageously identify the glycogen store within a target muscle 106 as the glycogen itself likely varies in concentration within the target muscle.

Further too, it will be observed that the non-muscle tissue 208 varies from location to location as between FIGS. 6-9. Moreover the methods and or use of SNDGS 100 can provide a non-invasive determination of glycogen stores within a target muscle 106 even as the scan of the target muscle 106 may vary somewhat from one scan to the next.

Moreover, at the second time interval $X_2$, as shown in the scan 700 of FIG. 7, the glycogen stores 502 in the deeper portion 750 of the target muscle 106 are still generally high. The glycogen stores 502 in the outer portion 752 of the target muscle 106 tissue are beginning to diminish. Indeed prior to the onset of testing of the methods disclosed herein, it was unknown as to whether glycogen stores depleted evenly throughout, from the outside in or the inside out.

Indeed, although a biopsy of the target muscle can be performed to detect glycogen stores, based on the preliminary findings from test applications of this method it is clear that even a biopsy could be misleading—for if the biopsy is taken from too deep or too shallow a location within the target muscle, the sample may or may not accurately represent an overall evaluation of the target muscle as a whole. For at least one embodiment where a biopsy is performed contemporaneously with the scan of a target muscle such as to establish a baseline for a given subject, the location of the biopsy within the scan is noted so as to correlate the results of the biopsy to a specific area of the scan and thereby permit relative valuation to the other areas of the scan, e.g., areas 602, 702, 802, 902 based on the results of the biopsy.

Advantageously, and quite distinct from the biopsy, as the entire method is performed as a non-invasive process, there is no insult to the target muscle and therefore no real prospect of the test itself hampering performance. Further still, it is possible to quickly and easily compare in near real time the glycogen stores of different muscles, e.g. the subjects right rectus femoris muscle and the subjects left rectus femoris muscle. Such information may be highly advantageous during the rehabilitation of a muscle or group of muscles.

In other words, the method and or use of SNDGS 100 can enhance the evaluation of glycogen stores within the target muscle that cannot easily be achieved, if at all matched strictly with muscle biopsy.

As with FIG. 6 a grid 600 has been applied to the scan 700 to define a plurality of areas 702 within the scan 700. Glycogen stores 502 are again represented as dots of varying sizes. Undesirable areas, of which area 704 is exemplary, are again removed from consideration as indicated by the circle-X.

In accordance with the application of method 400, an area, such as exemplary area 706 is selected and the attributes of this area 706 are compared to the glycogen concentration scale 506 and an appropriate value assigned to area 706, blocks 414 and 416. For example, exemplary area 706 is quantified as a 3 whereas exemplary area 708 is quantified as a 4.

Again, method 400 proceeds with a query as to whether there are remaining areas to be quantified, decision 418. If additional areas remain, a new area is selected, block 402 and the attribute(s) are again quantified, block 416.

As in FIG. 6, with the attributes of all areas now quantified as values, the values are processed to determine a glycogen store for the target muscle 106 as indicated by scan 700. In at least one embodiment the processing of the values is averaging the values. Moreover, in FIG. 7 a table 710 is shown with columns A~L and rows 1~12 correlating to the defined areas 702 of scan 700. The quantified values of the selected attribute for each area are shown and the overall average is shown to be 2.99, and indeed a reduction from the scan 500 at time $X_1$.

In FIG. 8 representing scan 800 at time interval $X_3$, brief observation indicates that both the deeper portion 850 and the outer portion 852 of the target muscle 106 are showing decreased glycogen stores 502.

As with FIGS. 6 and 7 a grid 600 has been applied to the scan 800 to define a plurality of areas 802 within the scan 800. Undesirable areas, of which area 804 is exemplary are again removed from consideration as indicated by the circle-X.

Again in accordance with the application of method 400, an area, such as exemplary area 806 is selected and the attributes of this area 806 are compared to the glycogen concentration scale 506 and an appropriate value assigned to area 806. For example, exemplary area 806 is quantified as a 2 whereas exemplary area 808 is quantified as a 1.

Again, method 400 proceeds with a query as to whether there are remaining areas to be quantified, decision 418. If additional areas remain, a new area is selected, block 402 and the attribute(s) are again quantified, block 416.

As in FIGS. 6 and 7, with the attributes of all areas now quantified as values, the values are processed to determine a glycogen store for the target muscle 106 as indicated by scan 800. In at least one embodiment the processing of the values is averaging the values. Moreover, in FIG. 8 a table 810 is shown with columns A~L and rows 1~12 correlating to the defined areas 802 of scan 800. The quantified values of the selected attribute for each area are shown and the overall average is shown to be 1.8, and indeed a reduction from the scan 700 at time $X_2$.

In FIG. 9 representing scan 900 at time interval $X_4$, brief observation indicates once again that both the deeper portion 950 and the outer portion 952 of the target muscle 106 are showing decreased glycogen stores 502.

Once again, as with FIGS. 6, 9 and 8 a grid 600 has been applied to the scan 900 to define a plurality of areas 902 within the scan 900. Undesirable areas, of which area 904 is exemplary are again removed from consideration as indicated by the circle-X.

Again in accordance with the application of method 400, an area, such as exemplary area 906 is selected and the attributes of this area 906 are compared to the glycogen concentration scale 506 and an appropriate value assigned to area 906. For example, exemplary area 906 is quantified as a 0 whereas exemplary area 908 is quantified as a 1.

Again, method 400 proceed with a query as to whether there are remaining areas to be quantified, decision 418. If additional areas remain, a new area is selected, block 402 and the attribute(s) are again quantified, block 416.

As in FIGS. 6, 7 and 8 with the attributes of all areas now quantified as values, the values are processed to determine a glycogen store for the target muscle 106 as indicated by scan 900. In at least one embodiment the processing of the values is averaging the values. Moreover, in FIG. 9 a table 910 is shown with columns A~L and rows 1~12 correlating to the defined areas 902 of scan 900. The quantified values of the selected attribute for each area are shown and the overall average is shown to be 0.54, and indeed an even further reduction from the scan 800 at time $X_3$.

With respect to FIGS. 6-9, it is understood and appreciated that as substantially the same grid 600 is applied to each scan, e.g., scans 500, 700, 800 and 900, the same number of areas are defined within each scan, and the size of the defined areas is generally constant from one scan to the next. This consistency remains and is not affected by different locations of the scan. Certainly for consistency it is desirable for the operator to attempt to be close and perform each scan in approximately the same location—but slight variation of location is not detrimental.

Figure 10:
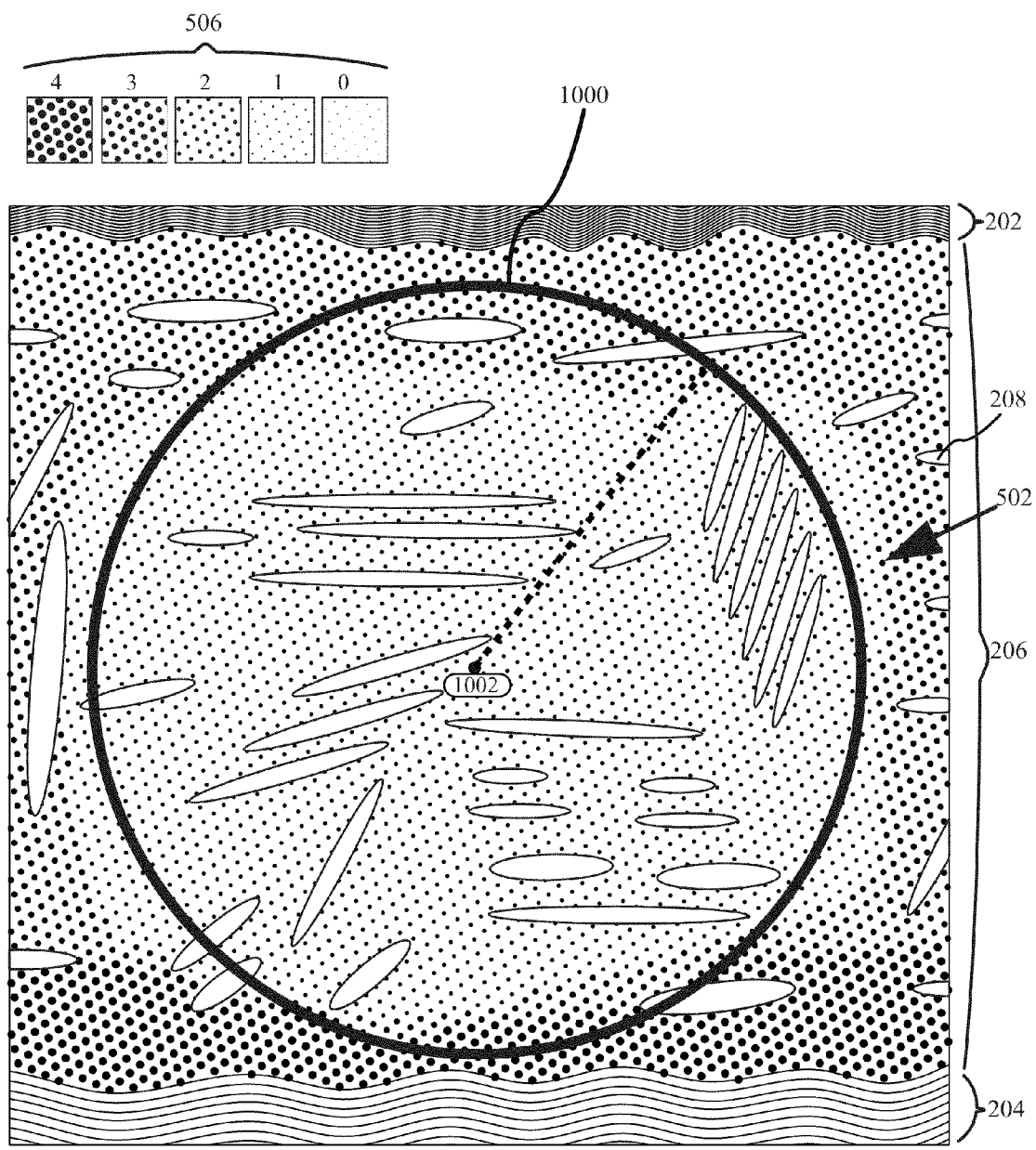
FIG. 10 is a conceptual illustration of an ultrasound scan of a target muscle further showing an automated selection of an area for evaluation in accordance with at least one embodiment.

In addition, in FIGS. 6-9 and with respect to the evaluating operation of method 400, it has been noted above that undesirable areas are removed from consideration. In at least one embodiment, the selection of the subset of areas for quantified valuation is an automated process. More specifically, as shown in FIG. 10, in at least one embodiment the selection of the portion 1000 for evaluation is determined based upon the center 1002 of the scanned image of the target muscle 106. In alternative embodiments the portion 1000 could also be offset from the determination of the skin and outer tissue layers or by other generally established reference point.

Figure 11:
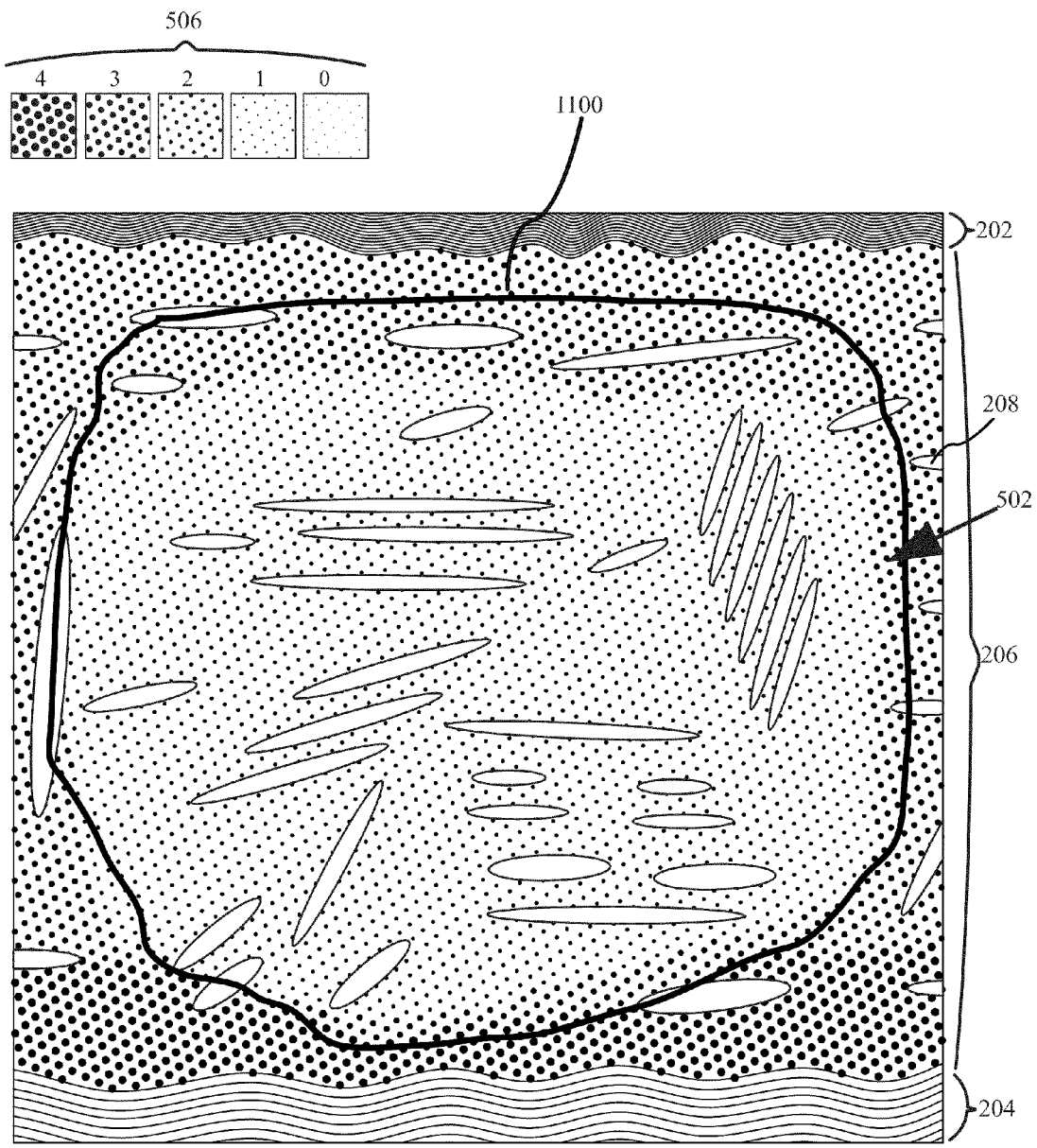
FIG. 11 is a conceptual illustration of an ultrasound scan of a target muscle further showing a user adjusted/determined selection of an area for evaluation in accordance with at least one embodiment.

In at least one alternative embodiment, the selection of the portion for evaluation is user adjustable and or definable. More specifically, for at least one embodiment as shown in FIG. 11, the operator can indicate by a drawn line 1100 the boundary for the selected portion for evaluation. In yet other alternative embodiments, line 1100 may be achieved by stretching and otherwise altering the initial automated selection, such as portion 1000 in FIG. 10.

Figure 12:
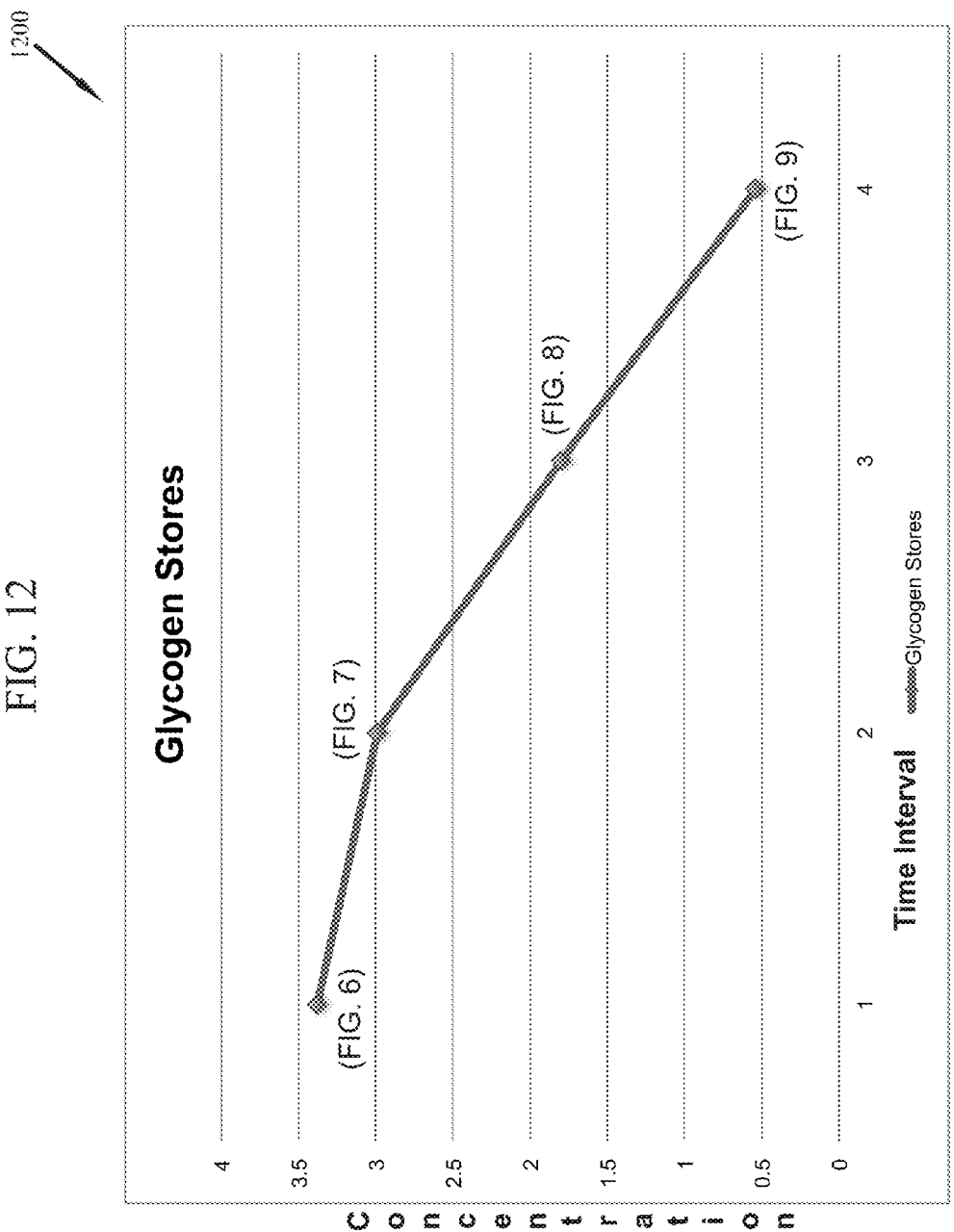
FIG. 12 is a chart of the determined glycogen stores as determined in FIGS. 6, 7, 8 and 9 in accordance with at least one embodiment.

FIG. 12 presents a chart 1200 of the determined glycogen stores for times $X_1 \sim X_4$ as shown in FIGS. 6~9. Such testing and the resulting chart 1200 can be an advantageous tool in athlete conditioning. For example, use of the method and or SNDGS 100 prior to the onset of training and during training can assist the athlete subject in maximizing his or her training efforts, for attempting to exercise or compete with diminished glycogen stores can accelerate muscle breakdown, increase the possibility of injury, and potentially subject the subject to other undesirable conditions.

Moreover, application of the methods and or SNDGS 100 can help determine whether the subject should eat more carbohydrates before exercising or competing, whether his or her glycogen stores are good and further eating would only divert blood from the muscles to the stomach for digestion, and or whether despite eating the subject's muscles are not in an optimal condition for exercise or competition and rest should be enjoyed.

Further, as SNDGS 100 permits substantially real time analysis of glycogen stores, a base line for a subject's metabolism and conversion of foods to glycogen stores can be established. More specifically, by having a subject eat food, such as but not limited to bread, fruit, energy supplements such as gels, formulated bars, etc. . . . and scanning one or more target muscles during and after the consumption, SNDGS 100 permits the subject to advantageously know his or her precise conversion scale for "X" grams of carbohydrates to a "Y" valuation of glycogen stores in a given amount of time.

Such knowledge of how many grams of carbohydrates equate to a maximum glycogen storage value, and/or the replenishment of that value is highly advantageous in many settings. A coach can monitor and adjust the food intake of his or her individual or team athlete(s), but so too can military personnel better prepare for mission critical situations. More specifically, by forecasting the duration of a mission and the level of exertion during that mission, a commander can accurately predict how much food each member of the team should have, for too little and the mission may suffer due to fatigue or lack of optimum performance and too much may adversely add unnecessary bulk and weight to a team that is striving to move with speed and stealth.

Moreover, SNDGS 100 and/or methods 300/350/400 are for at least one embodiment adapted as a method of endurance conditioning for a subject. Specifically, during periods of endurance activity a coach, therapist, trainer, or other person—including the subject, can scan one or more target muscles at a plurality of intervals. Typically the first interval would be just before starting or at about the onset of the activity. By tensing the target muscle as noted above, a great consistency for the scan and evaluation is easily achieved. Based on the scan and it's evaluation the endurance activity may be adjusted—such as to increase the level of activity, decrease the level of activity or perhaps even halt the endurance activity all together.

As the ultrasound scanning process is quick, and can be performed with hand held devices, discussed further below, SNDGS 100 and/or methods 300/350/400 can be performed in the filed of the endurance activity. In other words the subject does not have to travel to a specific facility or location for the scanning and evaluation to be performed. For example a cyclist can pause on a trainer or even hold onto a moving car to permit the scan of a target leg muscle. A swimmer may rest at the edge of the pool or hop out briefly to permit the scan of a target muscle. A runner may pause on a treadmill or stop on the side of the road. A football, soccer, or other field athlete may permit a scan while he or she is out of rotation. A patient undergoing rehab may be scanned during the rehab. Moreover, the glycogen levels of a subject may be non-invasively determined in a setting where such determination is highly advantageous and contemporaneously applicable to the performance of the endurance activity.

Returning to the FIGS. 5-9 and the evaluating operation as shown in FIG. 4, it is once again noted that throughout the muscle tissue 206 are elements of non-muscle tissue 208, such as but not limited to connective tissue, vascular tissue, scar tissue, foreign objects, etc. . . . In the initial review of method 400 it was noted that identifying and discounting of non-muscle tissue could be achieved and would likely enhance the precision for the determination of the glycogen store within the target muscle 106.

Returning to FIG. 4, and FIG. 6, in at least one embodiment this elimination of non-muscle tissue 208 is achieved through the application of a threshold in the area evaluation. For the initial pass, a threshold should to be set, decision 412. For at least one embodiment, the threshold may be a user provided value.

Establishing a threshold from the scan itself may be advantageous as the threshold is then self determined from the scan and can vary from scan to scan, muscle to muscle, subject to subject etc. . . . while still maintaining high precision for evaluation.

In at least one embodiment where the threshold is self determined from the scan, the method 430 of initializing the threshold substantially parallels the above description for the general determination of the glycogen value with respect to block 410—block 418.

Moreover, the method 430 proceeds to select an area 602 that has not been removed from further consideration, block 432. The attribute of this area 602 is then quantified as a value, block 434. More specifically the attribute of the selected area 602 is compared to the glycogen concentration scale 506 and an appropriate value assigned to the area 602. For example exemplary area 606 is quantified as a 4 whereas exemplary area 608 is quantified as a 2.

The method 430 of initializing the threshold proceeds with a query as to whether there are remaining areas to be quantified, decision 436. If additional areas remain, a new area is selected, block 438 and the attribute(s) are again quantified, block 416.

With the attributes of all areas now quantified as values, the values are processed to determine a glycogen store for the target muscle 106 as scanned and represented by scan 500, block 422. In at least one embodiment the processing of the values is averaging the values. Moreover, in FIG. 6 a table 612 is shown with columns A~L and rows 1~12 correlating to the defined areas 602 of scan 500. The quantified values of the selected attribute for each area are shown and the overall average is shown to be 3.38.

Although the threshold can be set to be the overall average, as different areas have different concentrations of glycogen due to the presence or absence of non-muscle tissue 208 as well as state of the muscle tissue itself, in general for at least one embodiment the threshold is established as a percentage of the initial average value, block 440, such as for example 80%. Moreover, for at least one embodiment, evaluated areas having an attribute value of at least 3.07 (80% of 3.38) are considered muscle tissue while areas having an attribute value of less than 3.07 (80% of 3.38) are considered non-muscle tissue 208 and therefore eliminated from further consideration.

With a threshold so established, as each area is quantified under block 416, the quantified value is now compared to the threshold, in accordance with method refinement 450. For an embodiment where the same threshold is to be applied for the entire scan, the previously determined threshold is used, decision 452 and block 454. As will be further explained momentarily, in at least one alternative embodiment the threshold is adaptively varied, and more specifically is based the values of proximate areas, decision 452 and block 456.

Where the value of the attribute is above the threshold, e.g., greater than 3.07 (80% of 3.38), decision 458, the area and its associated value is maintained, block 460. Where the value of the attribute is below the threshold, e.g. smaller than 3.07 (80% of 3.38), decision 458, the area and its associate value are discarded, block 462. Moreover it is understood and appreciated that the value of the attribute is compared to the threshold. Incidental variations of the method to keep the value if equal to or above in one embodiment or to discard if equal to or below in an alternative embodiment are within the scope of this methodology.

For the example of FIG. 6 there are nine (9) areas with evaluated attributes rated as 2. For ease of identification, these instances have been bolded and centered in table 612 Eliminating these nine values leaves ninety one remaining values that are above the threshold, and permits a refined glycogen store evaluation of 3.90.

Whereas FIGS. 5 and 6 conceptually show the glycogen stores within the muscle tissue to be generally uniform, FIGS. 7-9 conceptually show the glycogen stores within the muscle tissue as being more variable, as application of the methods has so determined in repeated testing. As such, it is advantageously beneficial for the threshold in at least one embodiment to be variable.

As suggested by the method refinement 450 for threshold evaluation, initially the threshold can be based on the previously determined general threshold for the entire scan. However, in at least one embodiment an adjustable cache for the values of areas proximate to the current area being evaluated is established. Until the cache is established, e.g., for the first few passes of evaluation, decision 452, the initial threshold value is used, block 454.

In varying embodiments this cache may be for areas in the same row (N elements before, after or on either side), areas in the same column (M elements above, below or on either side), areas in the same grid subsection (M elements by N elements including the currently selected area), and or combinations thereof. How the cache of proximate values is established—above, below, before, after, around—is largely dependent on how the areas of the scan are selected for evaluation. In addition, the number of values that may be maintained in the cache is at least in part determined by the defined size of each area.

With respect to the method refinement 450 for threshold evaluation, if the value is above the threshold, decision 458 the area and it's value are kept, but the value may also be added to the proximate value cache, consisting of N members. As new members are added, old members are discarded, and in this way the proximate value cache maintains a consistent record of values for proximate areas.

Moreover, when the next area is selected, block 420 of the evaluation operation method, as the proximate cache has been established, the threshold is based on the proximate value cache, block 456. As before, in at least one embodiment, the threshold is a percentage of the proximate value cache. By adopting a percentage, some degree of fluctuation between areas is permitted, but a sudden change will stand out as tissue substantially unlikely to be muscle tissue.

Figure 13:
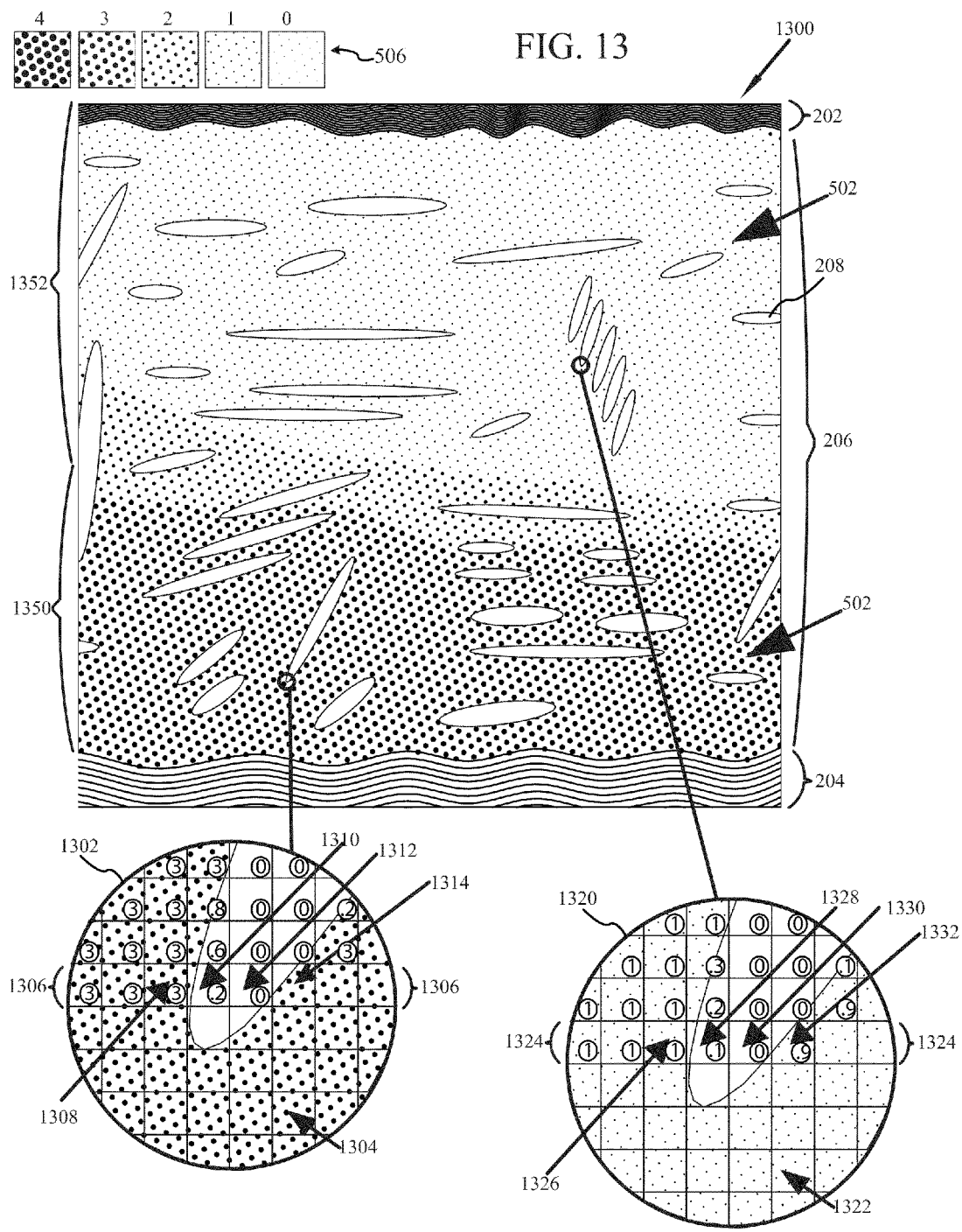
FIG. 13 is a conceptual illustration of an ultrasound scan of a target muscle further illustrating a first part having a first threshold value and a second part having a second threshold value in accordance with at least one embodiment.

FIG. 13 conceptually illustrates a scan 1300 of a target muscle 106. As with FIGS. 5-9, glycogen stores 502 within the muscle tissue 206 are represented as dots of varying sizes. As shown in scan 1300 the deeper portion 1350 of the target muscle 106 has a greater apparent glycogen store 502 then the outer portion 1352 of the target muscle. As such, if a constant threshold was applied in the evaluation, areas in the outer portion 1352 might be inadvertently discounted and areas of the deeper portion 1350 might be inadvertently included, and or vis-a-versa depending on the value of the threshold.

An enlarged first section 1302 is shown for the deeper portion 1350. Within this enlarged section a plurality of areas 1304 are shown. These areas include muscle tissue 206, but also in some instances non-muscle tissue 208. The scale of the areas is such that as shown each area is predominantly either muscle tissue 206 or non-muscle tissue 208. With respect to the glycogen concentration scale 506, the attributes of the areas of predominant muscle tissue are defined as "3" whereas the attributes of the areas of non-muscle tissue are defined as "0."

By way of example to demonstrate the application of the proximate cache value, attention is directed to example row 1306, and currently selected area 1308. The proximate value cache from the two areas immediately to the left of area 1308 are 3. As the attributes of area 1308 are also evaluated as a 3, the value of area 1308 is above the threshold, regardless of what percentage is used. Area 1308 and its value are then kept for the overall glycogen store determination and the value is also added to the proximate value cache, block 460. If the cache is full, the oldest value is discarded and the new value is added.

The selection of the next area is then area 1310. In this case the attributes are evaluated as, for example 0.2. If the threshold is set as 80% of the proximate value cache (e.g., 3), the threshold would be 2.4—well above the 0.2 of area 1310. Area 1310 is therefore discarded as being very likely non-muscle tissue 208, block 462. The same is true for the next area 1312. However, for the next area 1314 the attributes are evaluated as 2.8 (not shown on FIG. 13) which is above the threshold. Area 1314 is kept and the proximate value cache updated once again, block 460.

Moreover, with a sufficiently fine granularity of defined areas and a reasonable proximate value cache, non-muscle tissue 208 can be statistically identified and eliminated with a reasonable degree of accuracy.

Turning now to the enlarged second section 1320 for the outer section, it is clear that areas 1322 are of substantially the same size as areas 1304 shown in the enlarged first section 1302. It is also visually apparent that with respect to the glycogen concentration scale 506 the attributes of the areas of predominant muscle tissue for the enlarged second section 1320 are defined as "1" and again the attributes of the areas of non-muscle tissue are defined as "0."

To parallel the above example, for enlarged second section 1320 attention is directed to example row 1324, and currently selected area 1326. The proximate value cache from the two areas immediately to the left of area 1326 are 1. As the attributes of area 1326 are also evaluated as a 1, the value of area 1326 is above the threshold, regardless of what percentage is used. Area 1326 and its value are then kept for the overall glycogen store determination and the value is also added to the proximate value cache, block 460. If the cache is full, the oldest value is discarded and the new value is added.

The selection of the next area is then area 1328. In this case the attributes are evaluated as, for example 0.1. If the threshold is set as 80% of the proximate value cache (e.g., 1), the threshold would be 0.8. While the difference between the areas value and the threshold is not as great as the similar example of the enlarged first section 1302, it is still below the threshold and therefore discarded as being very likely non-muscle tissue 208, block 462. The same is true for the next area 1330. However, for the next area 1332 the attributes are evaluated as 0.9 which is above the threshold. Area 1332 is kept and the proximate value cache updated once again, block 460.

To summarize the threshold for the enlarged first section 1302 is 2.4 whereas the threshold for the enlarged second section 1320 is 0.8, and each threshold is effective for its proximate location. Moreover, for at least one embodiment, a first part 1302 of the scan 1300 of the target muscle 106 has a first threshold value and a second part 1320 of the scan 1300 of the target muscle 106 has a second threshold value. For each, the threshold value is determined from a cache of neighboring area attribute values.

With respect to applications of SNDGS 100 and or method 300/350/400, for training, conditioning, rehabilitation or other purpose, it should be understood and appreciated, that the glycogen stores of more than one target muscle 106 can be determined. Moreover, the same muscle type, e.g. rectus femoris, vastus lateralis, biceps, etc. . . . , may be targeted in both the left and right legs or left and right arms, chest or back for comparison, and or different muscles from different areas may be compared. Further still, for each muscle there is also generally a long axis and a short axis, i.e., parallel to the subject's leg or arm bone or perpendicular to the subject's leg or arm bone. In varying embodiments, long axis and short axis scans of the same target muscle may also be compared.

FIG. 14 conceptually illustrates charts from several additional applications of SNDGS 100 and or method 300/350/400. In FIG. 1400A, the first, second and third scans as evaluated show very little difference for the target muscle, indicating that the subject is not in a prime condition for continued training (e.g., the muscles are fatigued), and though he or she may feel fine, heavy exertion may indeed overtax the muscles, and a lesser workout or even rest may be preferable to continuing the current exercise routine.

In FIG. 1400B, a scan 1402 of a target muscle in a subject's left leg, e.g. left vastus lateralis, are plotted with the scan 1404 of a target muscle in the subject's right leg, e.g., right vastus lateralis which is shown to be similar but faster in depletion as the subject is undergoing rehabilitation.

In FIG. 1400C different target muscles are plotted together, such as the rectus femoris 1406 and vastus lateralis 1408 of a subject for comparison and review of how different muscles are or are not similarly depleting their respective glycogen stores during active use.

Figure 15:
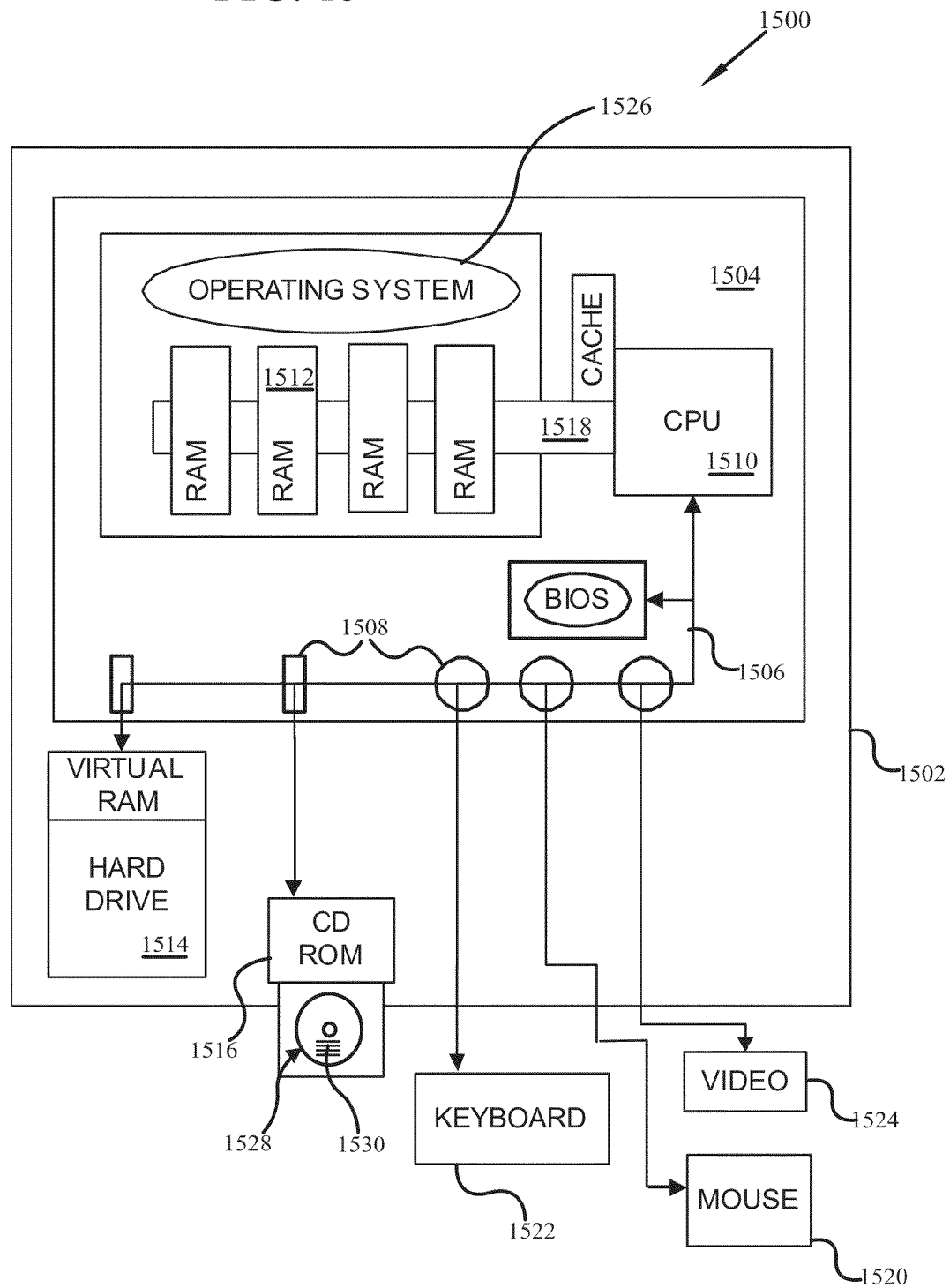
FIG. 15 is a block diagram of a computer system in accordance with at least one embodiment.

With respect to the above description of SNDGS 100 and methods 300, 350 and 400, it is understood and appreciated that the method may be rendered in a variety of different forms of code and instruction as may be preferred for different computer systems and environments. To expand upon the initial suggestion of a processor based device such as a computer 108 shown in FIG. 1 and discussed above, FIG. 15 is a high-level block diagram of an exemplary computer system 1500. Computer system 1500 has a case 1502, enclosing a main board 1504. The main board has a system bus 1506, connection ports 1508, a processing unit, such as Central Processing Unit (CPU) 1510 and a memory storage device, such as main memory 1512, and optionally a solid state drive or hard drive 1514 and/or CD/DVD ROM drive 1516.

Memory bus 1518 couples main memory 1512 to CPU 1510. A system bus 1506 couples hard drive 1514, CD/DVD ROM drive 1516 and connection ports 1508 to CPU 1510. Multiple input devices may be provided, such as for example a mouse 1520 and keyboard 1522. Multiple output devices may also be provided, such as for example a video display 1524 and a printer (not shown). In varying embodiments, the video display may also be a touch sensitive input device.

Computer system 1500 may be a commercially available system, such as a desktop workstation unit provided by IBM, Dell Computers, Gateway, Apple, Sun Micro Systems, or other computer system provider. Computer system 1500 may also be a smart phone or tablet computer such as an iPhone or iPad provided by Apple, the HP Slate, the Augen or Archos Android tablets, the Motorola Xoom or other such device. Computer system 1500 may also be a networked computer system, wherein memory storage components such as hard drive 1514, additional CPUs 1510 and output devices such as printers are provided by physically separate computer systems commonly connected together in the network. Those skilled in the art will understand and appreciate that physical composition of components and component interconnections comprising computer system 1500, and select a computer system 1200 suitable for the schedules to be established and maintained.

When computer system 1500 is activated, preferably an operating system 1526 will load into main memory 1512 as part of the boot strap startup sequence and ready the computer system 1500 for operation. At the simplest level, and in the most general sense, the tasks of an operating system fall into specific categories—process management, device management (including application and user interface management) and memory management.

In such a computer system 1500, the CPU 1510 is operable to perform one or more of the methods of non-invasive determination of glycogen stores as described above. Those skilled in the art will understand that a computer-readable medium 1528 on which is a computer program 1530 for non-invasive determination of glycogen stores may be provided to the computer system 1500. The form of the medium 1528 and language of the program 1530 are understood to be appropriate for computer system 1500. Utilizing the memory stores, such as for example one or more hard drives 1514 and main system memory 1512, the operable CPU 1502 will read the instructions provided by the computer program 1530 and operate to perform as SNDGS 100 as described above.

With respect to the various forms of the processor based device, such as the computer 108, further discussed and described as computer 1500, FIGS. 16-18 present alternative embodiments for the structural arrangement of components comprising SNDGS 100. More specifically, for alternative SNDGS 1600 as shown in FIG. 16, the ultrasound transducer 126 is coupled directly to the computer 108, such that SNDGS 1600 is itself disposed adjacent to the target muscle 106 (not shown).

For alternative SNDGS 1700 shown as FIG. 17, a dedicated processor based device such as a customized computer 1702 is provided, as opposed to adapting a pre-existing smart phone, tablet computer or other computer system. For SNDGS 1700, the display 116 of SNDGS 1600 is not shown so as to illustrate that alternative output devices such as an indicator 1704, lights 1706, speaker 1708, vibrator 1710 and/or combinations thereof can provide an operator with an indication of the non-invasively determined glycogen store. As with SNDGS 1600, the ultrasound transducer 126 may be directly coupled to the customized computer 1702, or tethered by a communications link 1712—wireless or wired as shown.

Further, for yet other embodiments, the computer program 112 to adapt a computer 108 may be provided directly by enhanced ultrasound transducer 1800. More specifically, computer program 112 may be incorporated as part of the circuit structure 1802 of enhanced ultrasound transducer 1800 such that upon connection to computer 108, SNDGS 100 is provided.

As suggested above with respect to FIG. 1, the computer program 112 may also be provided by a non-portable media such as a disc 114 to a third party computer, such as computer 1804, providing an application platform such as but not limited to the Apple App Store. A user can then connect his or her computer 108, such as tablet computer 1806 to the third party computer 1804 by a network 1808 (wired or wireless) or other communication channel and obtain computer program 112 so as to adapt his or her computer 1806 to perform as SNDGS 100 when a scan of a target muscle is provided. In varying embodiments, this scan may be provided by coupling computer 1806 to ultrasound transducer 126 operated as described above, receiving a scan of a target muscle from internal storage 1810, or receiving a scan of a target muscle another computer system 1812 via wired or wireless network 1814, or other appropriate communication channel.

Moreover, embodiments of SNDGS 100/1600/1700 are intended for a wide range of subjects. In many instances the primary user of SNDGS 100/1600/1700 is a coach or trainer who utilizes SNDGS 100/1600/1700 as an advantageous tool, as he or she can scan target muscles in athletes during training and test in real time at and during competition, regulations permitting, to better ensure optimum performance. Likewise with respect to civilian or military medical care, a doctor, nurse, therapist, or caregiver may utilize SNDGS 100/1600/1700 to ensure that patents under his or her care are receiving a proper balance of carbohydrates and muscle stimulating exercise. Further, a military commander and/or training officer can utilize SNDGS 100/1600/1700 to forecast requirements so that operating members of a team during a mission have sufficient food resources. And of course use of embodiments of SNDGS 100/1600/1700 are not strictly limited to human beings. Indeed, horse trainers, zoo veterinarians and other parties may employ the use of embodiments of SNDGS 100/1600/1700 to non-invasively determine the glycogen stores of the animals entrusted to their care.

Changes may be made in the above methods, systems and structures without departing from the scope hereof. It should thus be noted that the matter contained in the above description and/or shown in the accompanying drawings should be interpreted as illustrative and not in a limiting sense. The following claims are intended to cover all generic and specific features described herein, as well as all statements of the scope of the present method, system and structure, which, as a matter of language, might be said to fall there between.

What is claimed is:

1. A non-invasive method of determining glycogen store value in about real time comprising:
   receiving a high frequency ultrasound scan of at least a portion of a target muscle; and
   evaluating with a processor at least a portion of the ultrasound scan to determine glycogen store value within the target muscle in about real time.

2. The method of claim 1, further comprising imaging a selected target muscle with an ultrasound device having a movable transducer to provide the ultrasound scan of at least a portion of the target muscle.

3. The method of claim 1, wherein the method is repeated over time upon the same target muscle to determine a range of glycogen stores.

4. The method of claim 1, wherein evaluating at least a portion of the ultrasound scan comprises:
   defining a plurality of areas within the ultrasound scan, each area having at least one attribute;
   for at least a subset of defined areas, quantifying each attribute as a value from a predetermined range of values; and
   processing the values to determine a glycogen store.

5. The method of claim 4, wherein processing the values is averaging the values to determine a glycogen store.

6. The method of claim 4, wherein a grid is imposed upon at least a portion of the ultrasound scan to define the plurality of areas.

7. The method of claim 4, wherein pre-existing elements of the ultrasound scan define the plurality of areas.

8. The method of claim 7, wherein the pre-existing elements are one or more scan pixels.

9. The method of claim 1, wherein the ultrasound scan is an image.

10. The method of claim 1, adapted as an athlete training method by providing about real-time muscle glycogen store values to avoid training or competition with diminished glycogen stores.

11. The method of claim 1, wherein the method is performed in the field and receiving the ultrasound scan and evaluating the scan to determine the glycogen store within the target muscle are performed about contemporaneously and provided to a subject in about real time so as to avoid muscle activity with diminished glycogen stores.

12. The method of claim 1, wherein the method is about contemporaneously performed on different target muscles of a subject.

13. A computing device including a processor configured to perform the method of determining glycogen store within a target muscle as presented in claim 1.

14. A non-invasive method of determining glycogen stores value in about real time comprising:
   providing an ultrasound device having a movable transducer, the transducer operable in a high frequency range;
   selecting a target muscle of a subject;
   adjusting the ultrasound device for a depth of scan appropriate for the selected target muscle;
   disposing the transducer proximate to the subject and perpendicular to the selected target muscle;
   scanning the selected target muscle by processing ultrasound reflection received by the transducer to provide at least a partial scan of the selected target muscle;
   selecting an area of the scan; and
   evaluating with a processor the selected area to determine glycogen store value within the target muscle in about real time.

15. The method of claim 14, wherein the method is repeated over time upon the same target muscle to determine a range of glycogen stores.

16. The method of claim 14, wherein the method is about contemporaneously performed on different target muscles of the same subject.

17. The method of claim 14, wherein an image is provided by correlating the scan to attributes selected from the group consisting of, luminance, color, contrast, and combinations thereof.

18. The method of claim 14, wherein the ultrasound device is adjusted to provide Gray Scale output.

19. The method of claim 14, wherein the selected area is automatically determined based upon the center of the scan.

20. The method of claim 14, wherein the high frequency range is between about 5 to 20 Megahertz.

21. The method of claim 14, wherein the depth of scan is between about 1 centimeter and about 7 centimeters.

22. The method of claim 14, wherein the depth of scan is adjusted by selecting a type of target muscle.

23. The method of claim 14, wherein a subject tenses the selected target muscle during the scan.

24. The method of claim 23, wherein the tensing of the selected target muscle minimizes compression of the target muscle due to disposing of the transducer.

25. The method of claim 14, wherein the evaluating includes evaluating the hypoechoic appearance of the selected area.

26. The method of claim 14, wherein the evaluating is a qualitative analysis.

27. The method of claim 14, wherein the evaluating is a quantitative analysis, at least one attribute of the selected area is compared to a predefined reference of glycogen store values.

28. The method of claim 27, wherein the predefined reference is pre-established for the subject being tested.

29. The method of claim 14, wherein the evaluating is performed about contemporaneously with the imaging of the selected target muscle and the selecting of the area.

30. The method of claim 14, wherein evaluating at least a portion of the ultrasound scan comprises:
defining a plurality of areas within the ultrasound scan, each area having at least one attribute;
quantifying each attribute as a value from a predetermined range of values; and
processing the values to determine a glycogen store.

31. The method of claim 30, wherein processing the values is averaging the values to determine a glycogen store.

32. The method of claim 30, wherein a grid is imposed upon at least a portion of the ultrasound scan to define the plurality of areas.

33. The method of claim 30, wherein pre-existing elements of the ultrasound scan define the plurality of areas.

34. The method of claim 33, wherein the pre-existing elements are one or more scan pixels.

35. The method of claim 14, wherein the transducer is placed in direct contact with the subject and aligned in a first instance to a longitudinal axis of the target muscle and in a second instance to a latitudinal axis of the target muscle.

36. A method of endurance conditioning for a subject comprising:
at a plurality of intervals during a period of endurance activity;
disposing a transducer of an adjustable ultrasonic device proximate to the subject and perpendicular to a selected target muscle, the ultrasonic device adjusted for a depth of scan appropriate for the target muscle;
scanning the selected target muscle by processing ultrasound reflection received by the transducer to provide at least a partial scan of the selected target muscle;
selecting an area of the scan;
evaluating with a processor the selected area to determine glycogen store within the target muscle in about real time and during the period of endurance activity; and
adjusting the endurance activity to maintain the subject's glycogen store level at or above a pre-defined minimum glycogen store level.

37. The method of claim 36, wherein the subject tenses the selected target muscle during the scan to reduce muscle compression by the ultrasound device.

38. The method of claim 36, wherein multiple target muscles are scanned at each interval.

39. The method of claim 36, wherein a first interval is at the onset of the endurance activity and subsequent intervals at about even time intervals thereafter.

40. The method of claim 36, wherein adjusting the endurance activity is halting further activity.

41. The method of claim 36, wherein future endurance activity is adjusted based on evaluated glycogen stores.

42. The method of claim 36, wherein the subject is selected from the group consisting of professional athletes, military personnel, persons undergoing rehabilitation and or combinations thereof.

43. The method of claim 36, wherein each interval of disposing the transducer, scanning the target muscle, selecting an area and evaluating the selected area is performed in less than about 5 minutes.

44. The method of claim 36, wherein the method is performed in the field where the endurance activity is being performed.

45. The method of claim 36, further including administering a known quantity of carbohydrates to the subject and measuring a time until a subsequent real-time scan and evaluation show an increase in the glycogen store of the target muscle.

46. The method of claim 36, wherein evaluating at least a portion of the ultrasound scan comprises:
defining a plurality of areas within the ultrasound scan, each area having at least one attribute;
for at least a subset of defined areas, quantifying each attribute as a value from a predetermined range of values; and
processing the values to determine a glycogen store in about real time.

47. A system for non-invasive determination of glycogen stores value in about real time comprising:
means for receiving an ultrasound scan of at least a portion of a target muscle;
means for defining a plurality of areas within the ultrasound scan, each area having at least one attribute;
means for quantifying each attribute as a value from a predetermined range of values; and
means for processing the values to determine a glycogen store value in about real time.

48. The system of claim 47, further comprising imaging means for imaging a selected target muscle with an ultrasound device having a movable transducer to provide the ultrasound scan of at least a portion of the target muscle.

49. The system of claim 47, wherein a grid is imposed upon at least a portion of the ultrasound scan to define the plurality of areas.

50. The system of claim 47, wherein pre-existing elements of the ultrasound scan define the plurality of areas.

* * * * *